(12) United States Patent
Hariri et al.

(10) Patent No.: US 7,928,280 B2
(45) Date of Patent: Apr. 19, 2011

(54) TREATMENT OF LEG ULCERS USING PLACENTA DERIVED COLLAGEN BIOFABRIC

(75) Inventors: Robert J. Hariri, Florham Park, NJ (US); Janice M. Smiell, Morristown, NJ (US)

(73) Assignee: Anthrogenesis Corporation, Cedar Knolls, NJ (US)

(*) Notice: Subject to any disclaimer, the term of this patent is extended or adjusted under 35 U.S.C. 154(b) by 4 days.

(21) Appl. No.: 11/485,840

(22) Filed: Jul. 12, 2006

(65) Prior Publication Data

US 2007/0021704 A1 Jan. 25, 2007

Related U.S. Application Data

(60) Provisional application No. 60/699,441, filed on Jul. 13, 2005.

(51) Int. Cl.
*A61F 13/00* (2006.01)
(52) U.S. Cl. ............ 602/48; 602/41; 128/889; 128/898; 424/443; 424/445
(58) Field of Classification Search .................... 602/48, 602/42; 424/443–449; 604/304–308
See application file for complete search history.

(56) References Cited

U.S. PATENT DOCUMENTS

| | | | |
|---|---|---|---|
| 2,801,008 A * | 7/1957 | Schmid .................... 210/444 |
| 4,420,339 A | 12/1983 | Kato | |
| 4,837,024 A * | 6/1989 | Michaeli .................... 424/446 |
| 5,436,135 A | 7/1995 | Tayot | |
| 5,486,359 A | 1/1996 | Caplan | |
| 5,635,517 A | 6/1997 | Muller | |
| 5,698,579 A | 12/1997 | Muller | |
| 5,798,368 A | 8/1998 | Muller | |
| 5,814,328 A | 9/1998 | Gunasekaran | |
| 5,874,448 A | 2/1999 | Muller | |
| 5,877,200 A | 3/1999 | Muller | |
| 5,929,117 A | 7/1999 | Muller | |
| 5,955,476 A | 9/1999 | Muller | |
| 6,261,549 B1 | 7/2001 | Fernandez | |
| 6,281,230 B1 | 8/2001 | Muller | |
| 6,316,471 B1 | 11/2001 | Muller | |
| 6,335,349 B1 | 1/2002 | Muller | |
| 6,380,239 B1 | 4/2002 | Muller | |
| 6,387,367 B1 | 5/2002 | Davis-Sproul | |
| 6,395,754 B1 | 5/2002 | Muller | |
| 6,403,613 B1 | 6/2002 | Man | |
| 6,458,810 B1 | 10/2002 | Muller | |
| 6,476,052 B1 | 11/2002 | Muller | |
| 6,555,554 B2 | 4/2003 | Muller | |
| 7,045,148 B2 | 5/2006 | Hariri | |
| 7,091,353 B2 | 8/2006 | Robarge | |
| 2002/0103542 A1 | 8/2002 | Bilbo | |
| 2003/0032179 A1 | 2/2003 | Hariri | |
| 2003/0045552 A1 | 3/2003 | Robarge | |
| 2003/0180269 A1 | 9/2003 | Hariri | |
| 2003/0203008 A1 * | 10/2003 | Gunasekaran ................. 424/442 |
| 2003/0235909 A1 | 12/2003 | Hariri | |
| 2004/0028660 A1 | 2/2004 | Hariri | |
| 2004/0048796 A1 * | 3/2004 | Hariri et al. ...................... 514/12 |
| 2005/0021141 A1 | 1/2005 | Bleyer et al. | |
| 2005/0079147 A1 * | 4/2005 | Delaey et al. .............. 424/78.08 |
| 2005/0096351 A1 | 5/2005 | Jaworsky | |
| 2005/0171616 A1 * | 8/2005 | Sung et al. ................. 623/23.72 |
| 2006/0084815 A1 | 4/2006 | Muller | |

FOREIGN PATENT DOCUMENTS

| | | |
|---|---|---|
| WO | WO98/03502 | 1/1998 |
| WO | WO98/54170 | 12/1998 |
| WO | WO02/059106 | 8/2002 |
| WO | WO03/087333 | 10/2003 |

OTHER PUBLICATIONS

Graham, *Med Device Technol* 9(1):18-22 (1998).
Hennink et al., *Adv Drug Deliv Rev* 54(1):13-36 (2004).
Nguyen et al., *Biomaterials* 23(22):4307-4314 (2002).
Peppas et al., *Eur J Pharm Biopharm* 50(1):27-46 (2000).
Schmedlen et al., Biomaterials 23:4325-4332 (2002).
Skelhorne et al., *Med Device Technol* 13(9):19-23 (2002).
PCT ISA/EP—International Search Report dated Jan. 23, 2007, for International Application No. PCT/US2006/027364, filed Jul. 12, 2006.
PCT ISA/EP—Written Opinion dated Jan. 23, 2007, for International Application No. PCT/US2006/027364, filed Jul. 12, 2006.
Mostow E.N. et al., 2005, "Effectiveness of an Extracellular Matrix Graft (Oasis Wound Matrix) in the Treatment of Chronic Leg Ulcers: A Randomized Clinical Trail," *Journal of Vascular Surgery*, St. Louis, MO., US, vol. 41(5):837-843.
Niezgoda J.A. et al., 2005, "Randomized Clinical Trial Comparing Oasis Would Matrix to Regranex Gel for Diabetic Ulcers," *Advances in Skin and Wound Care*, Lippincott Williams & Wilkins, Ambler, PA, US., vol. 18(5) Part 1, pp. 258-266.
Shun A. et al., 1983, "Human Amnion in the Treatment of Chronic Ulceration of the Legs," *Medical Journal of Australia*, Australian Medical Pub., Sydney, AU, vol. 2(6):279-283.
Ward D.J. et al., 1989, "The Healing of Chronic Venous Leg Ulcers with Prepared Human Amion," *British Journal of Plastic Surgery*, Churchill Livingston, GB, vol. 42:463-467. USPTO, Non-final Office Action dated Dec. 29, 2005 for U.S. Appl. No. 10/379,867.
USPTO, Final Office Action dated Aug. 22, 2006 for U.S. Appl. No. 10/379,867.
USPTO, Advisory Action dated Mar. 27, 2007 for U.S. Appl. No. 10/379,867.
USPTO Non-final Office Action dated Jan. 24, 2008 for U.S. Appl. No. 10/379,867.
USPTO, Non-final Office Action dated Jan. 23, 2009 for U.S. Appl. No. 10/379,867.
USPTO, Notice of Abandonment dated Aug. 6, 2009 for U.S. Appl. No. 10/379,867.

* cited by examiner

*Primary Examiner* — Kim M Lewis
(74) *Attorney, Agent, or Firm* — Jones Day

(57) ABSTRACT

The present invention provides a method of treating a leg ulcer comprising contacting the leg ulcer with a collagen biofabric. The leg ulcer may be a venous, arterial, diabetic or decubitus (pressure) ulcer. The invention further provides kits comprising one or more pieces of collagen biofabric for the treatment of a leg ulcer.

16 Claims, No Drawings

TREATMENT OF LEG ULCERS USING PLACENTA DERIVED COLLAGEN BIOFABRIC

This application claims benefit of U.S. Provisional Application Ser. No. 60/699,441, filed Jul. 13, 2005, which is hereby incorporated by reference herein in its entirety.

1. FIELD OF THE INVENTION

The present invention relates to methods and compositions for the treatment and repair of leg ulcers, particularly venous leg ulcers, using a placenta-derived collagen biofabric.

2. BACKGROUND OF THE INVENTION

Leg ulcers, which are breaks in the skin of the leg, especially around the ankles, and foot ulcers, are a persistent problem in certain patient populations, particularly affecting elderly, immobile, obese, under-exercised, diabetic or atherosclerotic patients. Chronic leg ulcers are persistent, non-healing or slow-healing wounds in which the body's healing process becomes stalled. The four most common types of leg ulcers are: venous leg ulcers, arterial leg ulcers, diabetic ulcers, and decubitus (pressure) ulcers.

Leg ulcers, particularly venous leg ulcers (also known as venous stasis ulcers), have been treated by application of a variety of skin substitutes or dressings. An example of a collagen dressing is OASIS®, an extracellular matrix product derived from porcine small intestine submucosa. APLIGRAF®, a living bi-layered skin substitute, comprises a dermal layer and an epidermal layer. ALLODERM®, a dermal matrix product, is a tissue derived from donated human skin. The skin substitutes, however, have disadvantages, including high expense, difficulty in handling, delicacy or difficulty in obtaining graft material.

Thus, despite the prevalence of leg ulcerations, particularly venous leg ulcerations, and the availability of types of graft materials, there exists a need for a method of healing leg ulcers using a relatively inexpensive, lightweight, readily-available, durable material that can facilitate healing of the ulcerated area.

3. SUMMARY OF THE INVENTION

The present invention provides methods of treating a leg ulcer, comprising contacting said ulcer with a collagen biofabric for a time sufficient to improve at least one aspect of the leg ulcer, or prevent or reduce the worsening of at least one aspect of a leg ulcer. In one embodiment, said contacting is for a time sufficient for at least one aspect of the leg ulcer to measurably improve compared to a leg ulcer not contacted with the collagen biofabric. In another specific embodiment, said contacting is for a time sufficient to prevent or reduce the worsening of at least one aspect of a leg ulcer, compared to a leg ulcer not contacted with the collagen biofabric. In another specific embodiment, said contacting comprises placing the collagen biofabric on the leg ulcer so that substantially all of the surface area of the biofabric contacts the leg ulcer. In another specific embodiment, said contacting comprises placing the collagen biofabric on a meshed skin graft covering a leg ulcer so that a plurality, or substantially all, of the interstices of the skin graft are in contact with the biofabric. In various embodiments, said leg ulcer can be, for example, a venous leg ulcer, arterial leg ulcer, diabetic leg ulcer, decubitus ulcer, or split thickness skin grafted ulcer or wound.

The preferred collagen biofabric is substantially dry, i.e., about 20% or less water by weight, and substantially retains the proteins of the amnion, chorion, or both in their native, unmodified conformations. In a specific embodiment, for example, the collagen biofabric is not protease-treated. In another specific embodiment, proteins within said collagen biofabric are not artificially chemically crosslinked, that is, the collagen biofabric is not fixed. In another specific embodiment, the collagen biofabric is substantially dry prior to said contacting. In another specific embodiment, said collagen biofabric is provided as a sheet, membrane, netting or webbing. In another specific embodiment, the collagen biofabric is diced or sheared such that it is flowable through a cannula or needle. In another specific embodiment, said collagen biofabric is mounted on a support. In a more specific embodiment, said support is a bandage.

In another specific embodiment, said collagen biofabric additionally comprises a bioactive compound not naturally-occurring in the collagen biofabric, or present in a different concentration than in collagen biofabric to which the bioactive compound has not been added. In a more specific embodiment, said bioactive compound is a small organic molecule, a mineral, a metal, an antibiotic, amino acid, pain medication, anti-inflammatory agent, cytokine, growth factor, enzyme inhibitor, kinase inhibitor, an anti-tumor agent, an anti-fungal agent, an anti-viral agent, an anti-infective agent, a wound sealant or a wound healing or sealing agent. In a more specific embodiment, said wound healing or sealing agent is platelet-derived growth factor (PDGF), transforming growth factor (TGF), lactoferrin, thymosin, hyaluronic acid (HA), fibrin, fibronectin or thrombin, or a combination thereof.

4. DETAILED DESCRIPTION OF THE INVENTION

4.1 Treatment of Leg Ulcers Using Collagen Biofabric

The present invention provides methods for the treatment of a leg ulcer using a collagen biofabric. In this context, "treatment of a leg ulcer" comprises contacting the leg ulcer with collagen biofabric for a time sufficient to improve at least one aspect of the leg ulcer, or to reduce the worsening of at least one aspect of the leg ulcer, as compared to a leg ulcer not contacted with collagen biofabric. As used herein, "aspect of the leg ulcer" includes objectively measurable parameters such as ulcer size, depth or area, degree of inflammation, ingrowth of epithelial and/or mesodermal tissue, gene expression within the ulcerated tissue that is correlated with the healing process, quality and extent of scarring etc., and subjectively measurable parameters, such as patient well-being, perception of improvement, perception of lessening of pain or discomfort associated with the ulcer, patient perception that treatment is successful, and the like.

Thus, in a preferred embodiment, the invention provides a method of treating a leg ulcer comprising contacting the leg ulcer with collagen biofabric for a sufficient time to heal the ulcer, e.g., for a time sufficient for the epithelium to close over the ulcer. In another preferred embodiment, the leg ulcer is contacted with collagen biofabric for a time sufficient for at least one aspect of the leg ulcer to show measurable improvement, compared to a leg ulcer not contacted with collagen biofabric. In another embodiment, the leg ulcer is contacted with collagen biofabric for a time sufficient to prevent, or reduce, the worsening of at least one aspect of the leg ulcer, compared to a leg ulcer not contacted with the collagen biofabric.

Generally, the collagen biofabric is contacted with the leg ulcer in any manner that maximizes contact between the leg ulcer and collagen biofabric. For example, the collagen biofabric can be laid or pressed gently as a dry sheet on the leg ulcer, and can be allowed to adhere to the leg ulcer by contact alone. The dry sheet may optionally then be wetted so that the collagen biofabric additionally adheres to the skin surrounding the ulcer. In another embodiment, the collagen biofabric can be pre-wetted, for example with a saline solution, and laid or pressed gently onto the leg ulcer. As in the previous embodiment, the biofabric can be allowed to adhere to the leg ulcer without external means of securing the biofabric. In another embodiment, the leg ulcer and collagen biofabric can be covered by a bandage such that the collagen biofabric is pressed onto the surface of the leg ulcer. In a specific embodiment, the collagen biofabric can be attached to, or adhered to, the bandage. The collagen biofabric may, less preferably, be sutured, glued or stapled to tissue surrounding the leg ulcer. During the course of treating a leg ulcer, collagen biofabric may be applied a plurality of times. For example, when collagen biofabric contacted with a leg ulcer becomes absorbed into the ulcer, or otherwise degraded, the leg ulcer can be contacted with a fresh piece of the collagen biofabric. Preferably, the collagen biofabric covers all or substantially all of the surface of the leg ulcer.

In preparation for, and during, contacting a leg ulcer with collagen biofabric, the ulcer is preferably kept moist. Dry ulcers can be wetted with, e.g., a saline solution prior to contacting with the collagen biofabric.

The invention provides for the treatment of a leg ulcer using collagen biofabric at any point in the development and pathogenesis and/or healing of the ulcer.

Venous Leg Ulcers

The invention provides for the treatment of venous leg ulcers using collagen biofabric. Venous leg ulcers, also known as venous stasis ulcers or venous insufficiency ulcers, a type of chronic or non-healing wound, are widely prevalent in the United States, with approximately 7 million people, usually the elderly, afflicted. Worldwide, it is estimated that 1-1.3% of individuals suffer from venous leg ulcers. Approximately 70% of all leg ulcers are venous ulcers. Venous leg ulcers are often located in the distal third of the leg known as the gaiter region, and typically on the inside of the leg. The ulcer is usually painless unless infected. Venous leg ulcers typically occur because the valves connecting the superficial and deep veins fail to function properly. Failure of these valves causes blood to flow from the deep veins back out to the superficial veins. This inappropriate flow, together with the effects of gravity, causes swelling and progression to damage of lower leg tissues.

Patients with venous leg ulcers often have a history of deep vein thrombosis, leg injury, obesity, phlebitis, prior vein surgery, and lifestyles that require prolonged standing. Other factors may contribute to the chronicity of venous leg ulcers, including poor circulation, often caused by arteriosclerosis; disorders of clotting and circulation that may or may not be related to atherosclerosis; diabetes; renal (kidney) failure; hypertension (treated or untreated); lymphedema (buildup of fluid that causes swelling in the legs or feet); inflammatory diseases such as vasculitis, lupus, scleroderma or other rheumatological conditions; medical conditions such as high cholesterol, heart disease, high blood pressure, sickle cell anemia, or bowel disorders; a history of smoking (either current or past); pressure caused by lying in one position for too long; genetics (predisposition for venous disease); malignancy (tumor or cancerous mass); infections; and certain medications.

Venous ulcers are typically treated with wound debridement and with compression of the leg to minimize edema or swelling. Compression treatments include wearing therapeutic compression stockings, multilayer compression wraps, or wrapping an ACE bandage or dressing from the toes or foot to the area below the knee. An Unna boot may be used, but is less preferred.

Thus, in another embodiment, the invention provides a method of treating a venous leg ulcer comprising contacting the venous leg ulcer with collagen biofabric and applying compression to the venous leg ulcer, for a time sufficient to improve at least one aspect of the venous leg ulcer, or to lessen the worsening of at least one aspect of a venous leg ulcer, as compared to a venous leg ulcer not contacted with collagen biofabric. In a specific embodiment, said compression is applied by a therapeutic compression stocking, multilayer compression wrap, ACE bandage, or Unna boot. In a specific embodiment, the ulcer is debrided prior to contacting with the collagen biofabric. In another specific embodiment, the method additionally comprises treating an underlying cause of the venous leg ulcer.

Other Leg Ulcer Types

Arterial leg ulcers are caused by an insufficiency in one or more arteries' ability to deliver blood to the lower leg, most often due to atherosclerosis. Arterial ulcers are usually found on the feet, particularly the heels or toes, and the borders of the ulcer appear as though they have been 'punched out'. Arterial ulcers are frequently painful. This pain is relieved when the legs are lowered with feet on the floor as gravity causes more blood to flow into the legs. Arterial ulcers are usually associated with cold white or bluish, shiny feet.

The treatment of arterial leg ulcers contrasts to the treatment of venous leg ulcers in that compression is contraindicated, as compression tends to exacerbate an already-poor blood supply, and debridement is limited, if indicated at all. Thus, in another embodiment, the invention provides a method of treating an arterial leg ulcer comprising treating the underlying cause of the arterial leg ulcer, e.g., arteriosclerosis, and contacting the arterial leg ulcer with collagen biofabric for a time sufficient to improve at least one aspect of the arterial leg ulcer, or to lessen the worsening of at least one aspect of the arterial leg ulcer, as compared to an arterial leg ulcer not contacted with collagen biofabric. In a specific embodiment, the method of treating does not comprise compression therapy.

Diabetic foot ulcers are ulcers that occur as a result of complications from diabetes. Diabetic ulcers are typically caused by the combination of small arterial blockage and nerve damage, and are most common on the foot, though they may occur in other areas affected by neuropathy and pressure. Diabetic ulcers have characteristics similar to arterial ulcers but tend to be located over pressure points such as heels, balls of the feet, tips of toes, between toes or anywhere bony prominences rub against bed sheets, socks or shoes.

Treatment of diabetic leg ulcers is generally similar to the treatment of venous leg ulcers, though generally without compression; additionally, the underlying diabetes is treated or managed. Thus, in another embodiment, the invention provides a method of treating a diabetic leg ulcer comprising treating the underlying diabetes, and contacting the diabetic leg ulcer with collagen biofabric for a time sufficient to improve at least one aspect of the diabetic leg ulcer, or to lessen the worsening of at least one aspect of the diabetic leg ulcer, as compared to a diabetic leg ulcer not contacted with collagen biofabric.

Decubitus ulcers, commonly called bedsores or pressure ulcers, can range from a very mild pink coloration of the skin, which disappears in a few hours after pressure is relieved on the area to a very deep wound extending into the bone. Factors known to be associated with the development of ulcers include advanced age, immobility, poor nutrition, and incontinence. Stage 1 decubitus ulcers exhibit nonblanchable erythema of intact skin. Stage 2 decubitus ulcers exhibit superficial or partial thickness skin loss. Stage 3 decubitus ulcers exhibit full thickness skin loss with subcutaneous damage. The ulcer extends down to underlying fascia, and presents as a deep crater. Finally, stage 4 decubitus ulcers exhibit full thickness skin loss with extensive destruction, tissue necrosis, and damage to the underlying muscle, bone, tendon or joint capsule.

After removing the pressure or abrasion that is the underlying cause of the decubitus ulcer, treatment generally involves keeping the area clean, promoting tissue regeneration, and removing dead tissue. Thus, in another embodiment, the invention provides a method of treating a decubitus leg ulcer comprising removing the pressure causing the decubitus ulcer, and contacting the decubitus leg ulcer with collagen biofabric for a time sufficient to improve at least one aspect of the decubitus leg ulcer, or to lessen the worsening of at least one aspect of the decubitus leg ulcer, as compared to a decubitus leg ulcer not contacted with collagen biofabric.

A preferred collagen biofabric for use in the methods of treatment of a leg ulcer, described herein, is a collagen-containing, placenta-derived amniotic and/or chorion membrane material used as a film, membrane, or sheet. A particularly preferred collagen biofabric is the vacuum-dried, non-fixed, non-protease-treated amniotic membrane material described in Hariri, U.S. Application Publication U.S. 2004/0048796, which is hereby incorporated in its entirety, and produced by the methods described therein, and herein (see Examples 1, 2).

The invention further encompasses treating a leg ulcer using collagen biofabric in conjunction with one or more therapies or treatments used in the course of treating a leg ulcer. The one or more additional therapies may be used prior to, concurrent with, or after use of the collagen biofabric. The collagen biofabric, and one or more additional therapies, may be used where the collagen biofabric alone, or the one or more additional therapies, alone, would be insufficient to measurably improve, maintain, or lessen the worsening of, one or more aspects of a leg ulcer. For example, the invention provides for the treatment of a leg ulcer comprising contacting the leg ulcer with a collagen biofabric, and treating the leg ulcer in another manner not comprising contacting the leg ulcer with a collagen biofabric, where the contacting and the treating the leg ulcer using an additional therapy together cause a measurable improvement in, maintenance of, or lessening of the worsening of, at least one aspect of a leg ulcer, as compared to a leg ulcer not contacted with a collagen biofabric. In specific embodiments, the one or more additional therapies comprise, without limitation, treatment of the leg ulcer with a wound healing agent (e.g., PDGF, REGRANEX®); administration of an anti-inflammatory compound; administration of a pain medication; administration of an antibiotic; administration of an anti-platelet or anti-clotting medication; application of a prosthetic; application of a non-collagen biofabric dressing (e.g., moist to moist dressings; hydrogels/hydrocolloids; alginate dressings; collagen-based wound dressings; antimicrobial dressings; composite dressings; synthetic skin substitutes, etc.), and the like. In another embodiment, the additional therapy comprises contacting the leg ulcer with honey. For any of the above embodiments, in a specific embodiment, the leg ulcer is a venous leg ulcer, a decubitus ulcer, a diabetic ulcer, or an arterial leg ulcer.

In another specific embodiment, the additional therapy is a pain medication. The invention thus provides a method of treating a leg ulcer comprising contacting the leg ulcer with a collagen biofabric, and administering a pain medication to lessen or eliminate leg ulcer pain. In a specific embodiment, the pain medication is a topical pain medication.

In another specific embodiment, the additional therapy is an anti-infective agent. Preferably, the anti-infective agent is one that is not cytotoxic to healthy tissues surrounding and underlying the leg ulcer; thus, compounds such as iodine and bleach are disfavored. Thus, treatment of the leg ulcer, in one embodiment, comprises contacting the leg ulcer with collagen biofabric and administering an anti-infective agent. The anti-infective agent may be administered by any route, e.g., topically, orally, buccally, intravenously, intramuscularly, anally, etc. In a specific example, the anti-infective agent is an antibiotic, a bacteriostatic agent, antiviral compound, a virustatic agent, antifungal compound, a fungistatic agent, or an antimicrobial compound. In another specific embodiment, the anti-infective agent is ionic silver. In a more specific embodiment, the ionic silver is contained within a hydrogel. In a preferred embodiment, the collagen biofabric is impregnated with silver ions prior to application to the leg ulcer. In another embodiment, the collagen biofabric is impregnated with silver ions after application of the biofabric to the leg ulcer. In specific embodiments, the leg ulcer is a venous leg ulcer, arterial leg ulcer, decubitus ulcer, or diabetic ulcer.

The invention further provides a method of treating a leg ulcer comprising contacting the leg ulcer with collagen biofabric and a plurality of stem or progenitor cells. In one embodiment, the collagen biofabric may be contacted with the stem or progenitor cells prior to contacting the leg ulcer with the collagen biofabric. For example, a sheet or piece of collagen biofabric may be prepared immediately prior to application on the venous leg ulcer by disposing on the surface of the collagen biofabric a solution of stem or progenitor cells and allowing the stem or progenitor cells sufficient time to attach to the collagen biofabric. The stem or progenitor cells, alternately, may be disposed onto the surface of the collagen biofabric about 30 minutes, 1, 2, 3, 4, 5, 6, 7, 8, 9, 10, 12, 14, 16, 18, 20, 22, 24 or more hours prior to application of the collagen biofabric onto the leg ulcer. In another embodiment, the collagen biofabric may be contacted with the stem or progenitor cells after application of the collagen biofabric to the leg ulcer. In another embodiment, a the invention provides a method of treating a venous leg ulcer comprising contacting the leg ulcer with a plurality of stem or progenitor cells, and contacting the leg ulcer with collagen biofabric co that the collagen biofabric covers the leg ulcer and stem or progenitor cells.

The number of stem or progenitor cells disposed onto the leg ulcer, or onto the surface of the collagen biofabric, in any embodiment may vary, but may be at least $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$; or may be no more than $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$ stem or progenitor cells. Thus, in specific embodiments, the invention provides a method of treating a leg ulcer comprising contacting said leg ulcer with, in either order, (a) collagen biofabric, and (b) a plurality of stem or progenitor cells comprising $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$; stem or progenitor cells. In other specific embodiments, the invention provides a method of treating a leg ulcer, in particular, a venous leg ulcer comprising contacting said leg ulcer with, in either order, (a) collagen biofabric, and (b) a plurality of stem or progenitor cells comprising no more than $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$; stem or progenitor cells. In a more specific embodiment, said plurality of stem cells comprises two or more different stem or progenitor cell types.

In one aspect, the invention provides a method of treating a leg ulcer, comprising contacting the leg ulcer with a collagen biofabric, wherein said collagen biofabric does not raise a detectable immune response to the collagen biofabric. In a specific embodiment, the leg ulcer is a venous leg ulcer, arterial leg ulcer, decubitus ulcer, or diabetic ulcer.

4.2 Collagen Biofabric
4.2.1 Description

The collagen biofabric used to treat a leg ulcer may be derived from the amniotic membrane of any mammal, for example, equine, bovine, porcine or catarrhine sources, but is most preferably derived from human placenta. In a preferred embodiment, the collagen biofabric is substantially dry, i.e., is 20% or less water by weight. In another preferred embodiment, the collagen biofabric retains the native tertiary and quaternary structure of the amniotic membrane, i.e., has not been protease-treated. In another preferred embodiment, the collagen biofabric contains no collagen and other structural proteins that have been artificially crosslinked, e.g., chemically crosslinked, that is, the preferred collagen biofabric is not fixed. A preferred collagen biofabric is the dried, non-fixed, non-protease-treated amniotic membrane material described in Hariri, U.S. Application Publication U.S. 2004/0048796, which is hereby incorporated in its entirety, and that is produced by the methods described therein, and herein (see Examples 1, 2). However, the methods of the present invention can utilize any placenta-derived collagen material made by any procedure.

In a preferred embodiment, the collagen biofabric used in the treatment of a leg ulcer is translucent. In other embodiments, the collagen biofabric is opaque, or is colored or dyed, e.g., permanently colored or dyed, using a medically-acceptable dyeing or coloring agent; such an agent may be adsorbed onto the collagen biofabric, or the collagen biofabric may be impregnated or coated with such an agent. In this embodiment, any known non-toxic, non-irritating coloring agent or dye may be used.

When the collagen biofabric is substantially dry, it is about $0.1$ g/cm$^2$ to about $0.6$ g/cm$^2$. In a specific embodiment, a single layer of the collagen biofabric is at least 2 microns in thickness. In another specific embodiment, a single layer of the collagen biofabric used to repair a tympanic membrane is approximately 10-40 microns in thickness, but may be approximately 2-150, 2-100 microns, 5-75 microns or 7-60 microns in thickness in the dry state.

In one embodiment, the collagen biofabric is principally composed of collagen (types I, III and IV; about 90% of the matrix of the biofabric), fibrin, fibronectin, elastin, and further contains glycosaminoglycans and proteoglycans. In other embodiments, non-structural components of the biofabric may include, for example, growth factors, e.g., platelet-derived growth factors (PDGFs), vascular-endothelial growth factor (VEGF), fibroblast growth factor (FGF) and transforming growth factor-β1. The composition of the collagen biofabric is thus ideally suited to encourage the migration of fibroblasts and macrophages, and thus the promotion of wound healing.

The collagen biofabric may be used in a single-layered format, for example, as a single-layer sheet or an un-laminated membrane. Alternatively, the collagen biofabric may be used in a double-layer or multiple-layer format, e.g., the collagen biofabric may be laminated. Lamination can provide greater stiffness and durability during the healing process. The collagen biofabric may be, for example, laminated as described below (see Section 4.2.7).

The collagen biofabric may further comprise collagen from a non-placenta source. For example, one or more layers of collagen biofabric may be coated or impregnated with, or layered with, purified extracted collagen. Such collagen may be obtained, for example, from commercial sources, or may be produced according to known methods, such as those disclosed in U.S. Pat. Nos. 4,420,339, 5,814,328, and 5,436,135, the disclosures of which are hereby incorporated by reference.

The collagen biofabric used to treat a leg ulcer may comprise one or more compounds or substances that are not present in the placental material from which the collagen biofabric is derived. For example, the collagen biofabric may be impregnated with a bioactive compound. Such bioactive compounds include, but are not limited to, small organic molecules (e.g., drugs), antibiotics (such as Clindamycin, Minocycline, Doxycycline, Gentamycin), hormones, growth factors, anti-tumor agents, anti-fungal agents, anti-viral agents, pain medications, anti-histamines, anti-inflammatory agents, anti-infectives including but not limited to silver (such as silver salts, including but not limited to silver nitrate and silver sulfadiazine), elemental silver, antibiotics, bactericidal enzymes (such as lysozyme), wound healing agents (such as cytokines including but not limited to PDGF, TGF; thymosin), hyaluronic acid as a wound healing agent, wound sealants (such as fibrin with or without thrombin), cellular attractant and scaffolding reagents (such as added fibronectin) and the like. In a specific example, the collagen biofabric may be impregnated with at least one growth factor, for example, fibroblast growth factor, epithelial growth factor, etc. The biofabric may also be impregnated with small organic molecules such as specific inhibitors of particular biochemical processes e.g., membrane receptor inhibitors, kinase inhibitors, growth inhibitors, anticancer drugs, antibiotics, etc. Impregnating the collagen biofabric with a bioactive compound may be accomplished, e.g., by immersing the collagen biofabric in a solution of the bioactive compound of the desired concentration for a time sufficient to allow the collagen biofabric to absorb and to equilibrate with the solution; by spraying the solution onto the biofabric; by wetting the biofabric with the solution, etc.

In other embodiments, the collagen biofabric may be combined with a hydrogel. Any hydrogel composition known to one skilled in the art is encompassed within the invention, e.g., any of the hydrogel compositions disclosed in the following reviews: Graham, 1998, *Med. Device Technol.* 9(1): 18-22; Peppas et al., 2000, *Eur. J. Pharm. Biopharm.* 50(1): 27-46; Nguyen et al., 2002, *Biomaterials*, 23(22): 4307-14; Henincl et al., 2002, *Adv. Drug Deliv. Rev* 54(1): 13-36; Skelhorne et al., 2002, *Med. Device. Technol.* 13(9): 19-23; Schmedlen et al., 2002, *Biomaterials* 23: 43256-32; all of which are incorporated herein by reference in their entirety. In a specific embodiment, the hydrogel composition is applied on the collagen biofabric, i.e., disposed on the surface of the collagen biofabric. The hydrogel composition for example, may be sprayed onto the collagen biofabric or coated onto the surface of the collagen biofabric, or the biofabric may be soaked, bathed or saturated with the hydrogel composition. In another specific embodiment, the hydrogel is sandwiched between two or more layers of collagen biofabric. In an even more specific embodiment, the hydrogel is sandwiched between two or more layers of collagen biofabric, wherein the edges of the two layers of biofabric are sealed so as to substantially or completely contain the hydrogel.

The hydrogels useful in the methods and compositions of the invention can be made from any water-interactive, or water soluble polymer known in the art, including but not limited to, polyvinylalcohol (PVA), polyhydroxyehthyl methacrylate, polyethylene glycol, polyvinyl pyrrolidone, hyaluronic acid, alginate, collagen, gelatin, dextran or derivatives and analogs thereof.

In some embodiments, the collagen biofabric of the invention comprises one or more bioactive compounds and is combined with a hydrogel. For example, the collagen biofabric can be impregnated with one or more bioactive compounds prior to being combined with a hydrogel. In other embodiments, the hydrogel composition is further impregnated with one or more bioactive compounds prior to, or after, being combined with a collagen biofabric of the invention, for example, the bioactive compounds described in Section 4.2.2, below.

4.2.2 Bioactive Compounds

The collagen biofabric used in the methods of the invention may comprise (e.g., be impregnated with or coated with) one or more bioactive compounds. As used herein, the term "bioactive compound" means any compound or molecule that causes a measurable effect on one or more biological systems in vitro or in vivo. Examples of bioactive compounds include, without limitation, small organic molecules (e.g., drugs), minerals, metals, antibiotics, antiviral agents, antimicrobial agents, anti-inflammatory agents, antiproliferative agents, cytokines, enzyme or protein inhibitors, antihistamines, and the like. In various embodiments, the collagen biofabric may be coated or impregnated with antibiotics (such as Clindamycin, Minocycline, Doxycycline, Gentamycin), hormones, growth factors, anti-tumor agents, anti-fungal agents, antiviral agents, pain medications (including Xylocaine®, Lidocaine, Procaine, Novocaine, etc.), antihistamines (e.g., diphenhydramine, Benadryl®, etc.), anti-inflammatory agents, anti-infectives including but not limited to silver (such as silver salts, including but not limited to silver nitrate and silver sulfadiazine), elemental silver, antibiotics, bactericidal enzymes (such as lysozome), wound healing agents (such as cytokines including but not limited to PDGF (e.g., Regranex®), TGF; thymosin), lactoferrin, hyaluronic acid as a wound healing agent, wound sealants (such as fibrin with or without thrombin), cellular attractant and scaffolding reagents (such as fibronectin), and the like, or combinations of any of the foregoing, or of the foregoing and other compounds not listed. Such impregnation or coating may be accomplished by any means known in the art, and a portion or the whole of the collagen biofabric may be so coated or impregnated.

The collagen biofabric, or composites comprising collagen biofabric, may comprise any of the compounds listed herein, without limitation, individually or in any combination. Any of the biologically active compounds listed herein, and others useful in the context of the sclera or eye, may be formulated by known methods for immediate release or extended release. Additionally, the collagen biofabric may comprise two or more biologically active compounds in different manners; e.g., the biofabric may be impregnated with one biologically active compound and coated with another. In another embodiment, the collagen biofabric comprises one biologically active compound formulated for extended release, and a second biologically active compound formulated for immediate release.

Wound healing, including the healing of leg ulcers, for example venous leg ulcers, requires adequate nutrition, particularly the presence of iron, zinc, arginine, vitamin C, arginine, and the like. Thus, the collagen biofabric may be impregnated or coated with a physiologically-available form of one or more nutrients required for wound healing. Preferably, the nutrient is formulated for extended release.

The collagen biofabric, or composite comprising collagen biofabric, may comprise an antibiotic; In certain embodiments, the antibiotic is a macrolide (e.g., tobramycin (Tobi®)), a cephalosporin (e.g., cephalexin (Keflex®)), cephradine (Velosef®)), cefuroxime (Ceftin®, cefprozil (Cefzil®), cefaclor (Ceclor®), cefixime (Suprax® or cefadroxil (Duricef®), a clarithromycin (e.g., clarithromycin (Biaxin)), an erythromycin (e.g., erythromycin (EMycin®)), a penicillin (e.g., penicillin V (V-CillinK® or Pen VeeK®)) or a quinolone (e.g., ofloxacin (Floxin®), ciprofloxacin (Cipro®) ornorfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In certain embodiments, the collagen biofabric may be coated or impregnated with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

In certain other embodiments, the collagen biofabric, or a composite comprising collagen biofabric, is coated or impregnated with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, methotrexate, colchicine, allopurinol, probenecid, sulfinpyrazone and benzbromarone.

In certain embodiments, the collagen biofabric, or a composite comprising collagen biofabric, is coated or impregnated with an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

The collagen biofabric, or a composite comprising collagen biofabric, may also be coated or impregnated with a cytokine receptor modulator. Examples of cytokine receptor modulators include, but are not limited to, soluble cytokine receptors (e.g., the extracellular domain of a TNF-α receptor or a fragment thereof, the extracellular domain of an IL-10 receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-10 antibodies, anti-IL-6 antibodies, anti-IL-8 antibodies (e.g., ABX-IL-8 (Abgenix)), and anti-IL-12 antibodies). In a specific embodiment, a cytokine receptor modulator is IL-4, IL-10, or a fragment thereof. In another embodiment, a cytokine receptor modulator is an anti-IL-1 antibody, anti-IL-6 antibody, anti-IL-12 receptor antibody, or anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

The collagen biofabric, or a composite comprising collagen biofabric, may also be coated or impregnated with a cytokine. Examples of cytokines include, but are not limited to, colony stimulating factor 1 (CSF-1), interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), insulin-like growth factor 1 (IGF-1), platelet derived growth factor (PDGF), erythropoietin (Epo), epidermal growth factor (EGF), fibroblast growth factor (FGF) (basic or acidic), granulocyte macrophage stimulating factor (GM-CSF), granulocyte colony stimulating factor (G-CSF), heparin binding epidermal growth factor (HEGF), macrophage colony stimulating factor (M-CSF), prolactin, and interferon (IFN), e.g., IFN-alpha, and IFN-gamma), lactoferrin, transforming growth factor alpha (TGF-α), TGFβ1, TGFβ2, tumor necrosis factor alpha (TNF-α), vascular endothelial growth factor (VEGF), hepatocyte growth factor (HGF), etc.

The collagen biofabric may also be coated or impregnated with a hormone. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins. Examples of β-interferons include, but are not limited to, interferon β1-a and interferon β1-b.

The collagen biofabric, or composite comprising collagen biofabric, may also be coated or impregnated with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The collagen biofabric, or a composite comprising collagen biofabric, may also be coated or impregnated with an immunomodulatory agent, including but not limited to methothrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. peptide mimetics, and antibodies (e.g., human, humanized, chimeric, monoclonal, polyclonal, Fvs, ScFvs, Fab or F(ab)₂ fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boeringer), IDEC-CE9.Is (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD1a antibodies (e.g., Xanelim (Genentech)), and anti-B7 antibodies (e.g., IDEC-114) (IDEC))) and CTLA4-immunoglobulin. In a specific embodiment, a T cell receptor modulator is a CD2 antagonist. In other embodiments, a T cell receptor modulator is not a CD2 antagonist. In another specific embodiment, a T cell receptor modulator is a CD2 binding molecule, preferably MEDI-507. In other embodiments, a T cell receptor modulator is not a CD2 binding molecule. The collagen biofabric comprising one or more such immunomodulatory agents is useful in treating, e.g., autoimmune conditions such as lupus or psoriasis, and vasculitic lesions.

The collagen biofabric, or composite comprising collagen biofabric, may also be coated or impregnated with a class of immunomodulatory compounds known as IMiDs®. As used herein and unless otherwise indicated, the term "IMiD®" and "IMiDs®" (Celgene Corporation) encompasses small organic molecules that markedly inhibit TNF-α, LPS induced monocyte IL1β and IL12, and partially inhibit IL6 production. Specific immunomodulatory compounds are discussed below.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). The entireties of each of the patents and patent applications identified herein are incorporated herein by reference. Immunomodulatory compounds do not include thalidomide.

Various immunomodulatory compounds contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds may be used in methods and compositions. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

Preferred immunomodulatory compounds include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

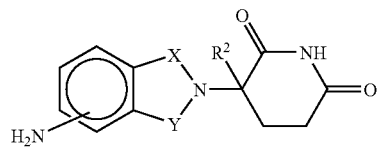

in which one of X and Y is C=O, the other of X and Y is C=O or CH$_2$, and R$^2$ is hydrogen or lower alkyl, in particular methyl. Specific immunomodulatory compounds include, but are not limited to:

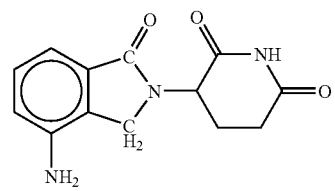

1-oxo-2-(2,6-dioxopiperidin-3-yl)-4-aminoisoindoline;

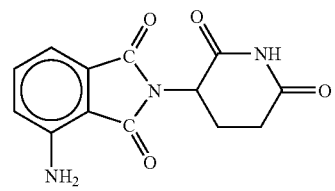

1,3-dioxo-2-(2,6-dioxopiperidin-3-yl)-4-aminoisoindoline; and

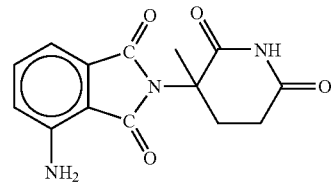

1,3-dioxo-2-(3-methyl-2,6-dioxopiperidin-3-yl)-4-aminoisoindole, and optically pure isomers thereof. The compounds can be obtained via standard, synthetic methods (see e.g., U.S. Pat. No. 5,635,517, incorporated herein by reference). The compounds are also available from Celgene Corporation, Warren, N.J.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzyl, or halo;
provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;
$R^2$ is H, F, benzyl, $(C_1-C_8)$alkyl, $(C_2-C_8)$alkenyl, or $(C_2-C_8)$alkynyl;
$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;
$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$C_1-C_6$)heterocycloalkyl, or $(C_0-C_4)$alkyl-$C_2-C_5$)heteroaryl;
$R^5$ is $(C_1-C_8)$alkyl, $(C_2-C_8)$alkenyl, $(C_2-C_8)$alkynyl, benzyl, aryl, or $(C_2-C_5)$heteroaryl;
each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;
n is 0 or 1; and
* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;
$R^2$ is H or $(C_1-C_8)$alkyl; and
$R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$C_2-C_5$)heteroaryl, $(C_5-C_8)$alkyl-N$(R^6)_2$; $(C_0-C_8)$alkyl-NH—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, R¹ is H, ($C_1$-$C_8$)alkyl, benzyl, $CH_2OCH_3$, $CH_2CH_2OCH_3$, or

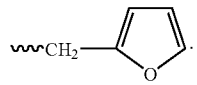

In another embodiment of the compounds of formula II, R¹ is

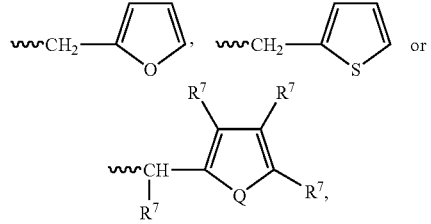

wherein Q is O or S, and each occurrence of $R^7$ is independently H, ($C_1$-$C_8$)alkyl, ($C_3$-$C_7$)cycloalkyl, ($C_2$-$C_8$)alkenyl, ($C_2$-$C_8$)alkynyl, benzyl, aryl, halogen, ($C_0$-$C_4$)alkyl-($C_1$-$C_6$)heterocycloalkyl, ($C_0$-$C_4$)alkyl-($C_2$-$C_5$)heteroaryl, ($C_0$-$C_8$)alkyl-N($R^6$)$_2$, ($C_1$-$C_8$)alkyl-$OR^5$, ($C_1$-$C_8$)alkyl-C(O)$OR^5$, ($C_1$-$C_8$)alkyl-O(CO)$R^5$, or C(O)$OR^5$, or adjacent occurrences of $R^7$ can be taken together to form a bicyclic alkyl or aryl ring.

In other specific compounds of formula II, $R^1$ is C(O)$R^3$.

In other specific compounds of formula II, $R^3$ is (C0-C4)alkyl-(C2-C5)heteroaryl, (C1-C8)alkyl, aryl, or ($C_0$-$C_4$)alkyl-$OR^5$.

In other specific compounds of formula II, heteroaryl is pyridyl, furyl, or thienyl.

In other specific compounds of formula II, $R^1$ is C(O)$OR^4$.

In other specific compounds of formula II, the H of C(O)NHC(O) can be replaced with ($C_1$-$C_4$)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

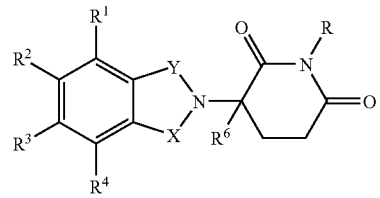

III and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
R is H or $CH_2OCR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—N($R^8R^9$);
$R^7$ is m-phenylene or p-phenylene or —($C_nH_{2n}$)— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;
$R^{10}$ is hydrogen, alkyl of to 8 carbon atoms, or phenyl; and
* represents a chiral-carbon center.
Other representative compounds are of formula:

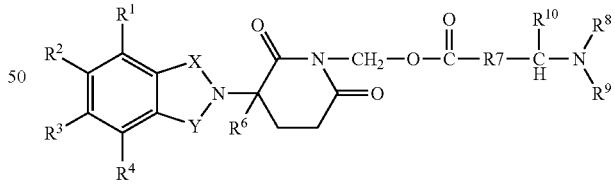

wherein:
one of X and Y is C=O and the other of X and Y is C=O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —($C_nH_{2n}$)— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and $R^{10}$ is hydrogen, alkyl of to 8 carbon atoms, or phenyl.

Other representative compounds are of formula:

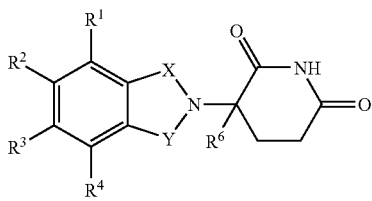

in which one of X and Y is C=O and the other of X and Y is C=O or $CH_2$;

each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and $R^6$ is hydrogen, alkyl of 1 to 8 carbon atoms, benzo, chloro, or fluoro.

Other representative compounds are of formula:

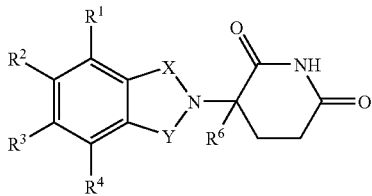

in which:

one of X and Y is C=O and the other of X and Y is C=O or $CH_2$;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen, alkyl of 1 to 8 carbon atoms, or CO—$R^7$—CH($R^{10}$)$NR^8R^9$ in which each of $R^7$, $R^8$, $R^9$, and $R^{10}$ is as herein defined; and $R^6$ is alkyl of 1 to 8 carbon atoms, benzo, chloro, or fluoro.

Specific examples of the compounds are of formula:

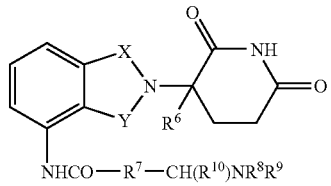

in which:

one of X and Y is C=O and the other of X and Y is C=O or $CH_2$;

$R^6$ is hydrogen, alkyl of 1 to 8 carbon atoms, benzyl, chloro, or fluoro;

$R^7$ is m-phenylene, p-phenylene or —$(C_nH_{2n})$— in which n has a value of 0 to 4; each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and $R^{10}$ is hydrogen, alkyl of 1 to 8 carbon atoms, or phenyl.

Preferred immunomodulatory compounds are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

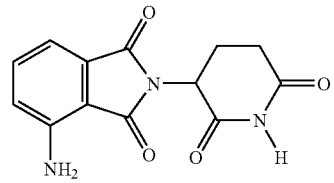

The compound 3-(4-amino-1-oxo-1,3-dihydro-isoindol-2-yl)-piperidine-2,6-dione has the following chemical structure:

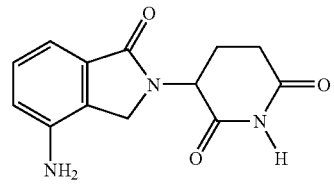

In another embodiment, specific immunomodulatory compounds encompass polymorphic forms of 3-(4-amino-1-oxo-1,3 dihydro-isoindol-2-yl)-piperidene-2,6-dione such as Form A, B, C, D, E, F, G and H, disclosed in U.S. provisional application No. 60/499,723 filed on Sep. 4, 2003, and U.S. non-provisional application Ser. No. 10/934,863, filed Sep. 3, 2004, both of which are incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C. Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds include, but are not limited to, 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

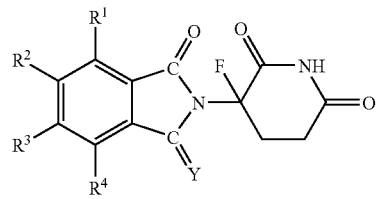

wherein:
Y is oxygen or $H^2$ and
each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds include, but are not limited to, the tetra substituted 2-(2,6-dioxopiperdin-3-yl)-1-oxoisoindolines described in U.S. Pat. No. 5,798,368, which is incorporated herein by reference. Representative compounds are of formula:

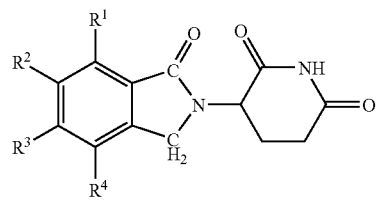

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

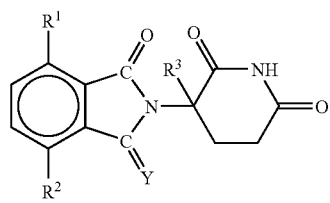

in which
Y is oxygen or $H_2$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and
$R^3$ is hydrogen, alkyl, or benzyl.

Specific examples of the compounds are of formula:

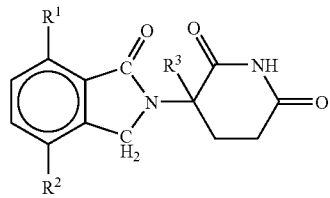

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

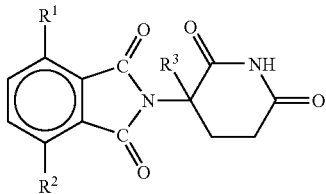

wherein:

a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;

the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl.

Other specific immunomodulatory compounds include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. Representative compounds are of formula:

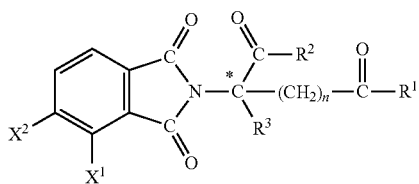

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

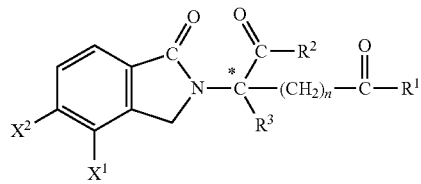

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

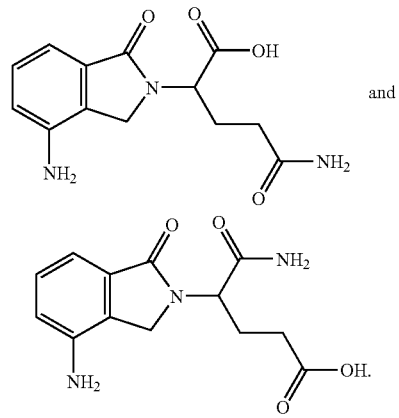

Other representative compounds are of formula:

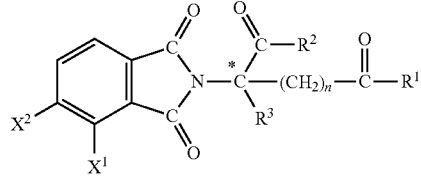

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2- yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptablesalts, solvate, prodrugs, and stereoisomers thereof:

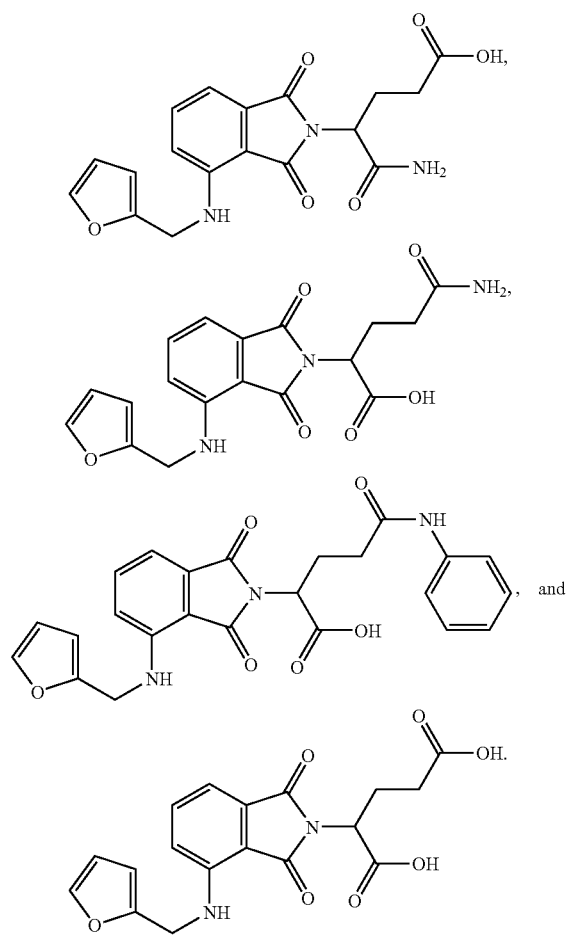

Other specific examples of the compounds are of formula:

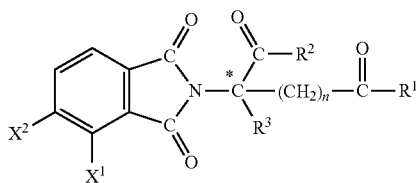

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Other representative compounds are of formula:

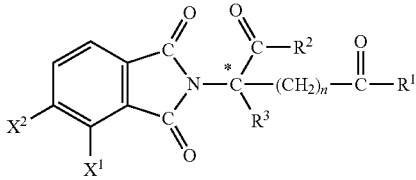

wherein:
one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Still other specific immunomodulatory compounds include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

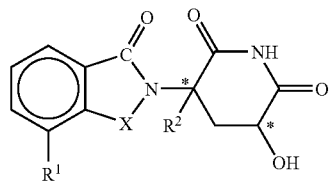

wherein:
the carbon atoms designated * constitute centers of chirality;
X is —C(O)— or —$CH_2$—;
$R^1$ is alkyl of 1 to 8 carbon atoms or —$NHR^3$;
$R^2$ is hydrogen, alkyl of 1 to 8 carbon atoms, or halogen; and
$R^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which
$R^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

The immunomodulatory compounds disclosed herein can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N dibenzylethylenediamine, chloroprocaine, choline, diethanolamine, ethylenediamine, meglumaine (N-methylglucamine), lysine, and procaine.

As used herein, and unless otherwise specified, the term "solvate" means a compound of the present invention or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds that comprise NO, NO2, ONO, or ONO2 moieties. Prodrugs can typically be prepared using well known methods, such as those described in 1 Burger's Medicinal Chemistry and Drug Discovery, 172 178, 949 982 (Manfred E. Wolff ed., 5th ed. 1995), and Design of Prodrugs (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this invention.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this invention (e.g., R/S=30/70, 35/65, 40/60, 45/55, 55/45, 60/40, 65/35 and 70/30). Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley Interscience, New York, 1981); Wilen, S. H., et al., Tetrahedron 33:2725 (1977); Eliel, E. L., Stereochemistry of Carbon Compounds (McGraw Hill, N.Y., 1962); and Wilen, S. H., Tables of Resolving Agents and Optical Resolutions p. 268 (E. L. Eliel, Ed., Univ. of Notre Dame Press, Notre Dame, Ind., 1972).

Compounds used in the invention may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The amount of the bioactive compound coating or impregnating the collagen may vary, and will preferably depend upon the particular bioactive compound to be delivered, and the effect desired. For example, where the bioactive compound is an anti-inflammatory agent, the amount of the anti-inflammatory agent on or contained by the collagen is an amount sufficient to measurably reduce one or more symptoms or indicia of inflammation in or around the leg ulcer.

In various embodiments, the collagen biofabric, used to treat a leg ulcer, may be coated with, or impregnated with, at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound. In another embodiment, the ocular plug of the invention may be coated with, or impregnated with, no more than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound.

4.2.3 Conformation of the Collagen Biofabric

The collagen biofabric may be formed into any shape or conformation that will facilitate its use in the methods of the invention. For example, the collagen biofabric can be formed in any shape or conformation that will facilitate the healing of a leg ulcer, e.g., a venous leg ulcer. For example, the collagen biofabric may be cut to various sizes so as to cover typical leg ulcers completely. The collagen biofabric may also be provided in various sizes so as to enable a physician, or other end user, to use or to cut an appropriately-sized piece for treatment of a leg ulcer, e.g., a venous leg ulcer. The collagen biofabric may be cut to a square, rectangular or oval shaped pieces, for example, or may be cut to conform to the shape of a particular ulcer on a particular patient. In various embodiments of the method, collagen biofabric pieces used to treat a leg ulcer, particularly a venous leg ulcer, may be approximately 1×1 cm, 1.5×1.5 cm, 2×2 cm, 2.5×2.5 cm, 3×3 cm, 3.5×3.5 cm, 4×4 cm, 4.5×4.5 cm, 5×5 cm, 1×1.5 cm, 1×2 cm, 1×2.5 cm, 1×3 cm, 1×3.5 cm, 1×4 cm, 1×4.5 cm, 1×5 cm, 1.5×2 cm, 1.5×2.5 cm, 1.5×3 cm, 1.5×3.5 cm, 1.5×4 cm, 1.5×4.5 cm, 2×2.5 cm, 2×3 cm, 2×3.5 cm, 2×4 cm, 2×4.5 cm, 2×5 cm, 2.5×3 cm, 2.5×3.5 cm, 2.5×4 cm, 2.5×4.5 cm, 2.5×5 cm, 3×3.5 cm, 3×4 cm, 3×4.5 cm, 3×5 cm, 3.5×4 cm, 3.5×4.5 cm, 3.5×5 cm, 4×4.5 cm, 4×5 cm, 4.5×5 cm in size, or up to 6×8 cm in size, or may be no smaller, or no larger, than 1×1 cm, 1.5×1.5 cm, 2×2 cm, 2.5×2.5 cm, 3×3 cm, 3.5×3.5 cm, 4×4 cm, 4.5×4.5 cm, 5×5 cm, 1×1.5 cm, 1×2 cm, 1×2.5 cm, 1×3 cm, 1×3.5 cm, 1×4 cm, 1×4.5 cm, 1×5 cm, 1.5×2 cm, 1.5×2.5 cm, 1.5×3 cm, 1.5×3.5 cm, 1.5×4 cm, 1.5×4.5 cm, 2×2.5 cm, 2×3 cm, 2×3.5 cm, 2×4 cm, 2×4.5 cm, 2×5 cm, 2.5×3 cm, 2.5×3.5 cm, 2.5×4 cm, 2.5×4.5 cm, 2.5×5 cm, 3×3.5 cm, 3×4 cm, 3×4.5 cm, 3×5 cm, 3.5×4 cm, 3.5×4.5 cm, 3.5×5 cm, 4×4.5 cm, 4×5 cm, or 4.5×5 cm, though the biofabric may be cut to different dimensions. Further, the biofabric used to treat a leg ulcer, particularly a venous leg ulcer, may be provided as a sheet from which an end use may cut two or more pieces, or may be provided as a roll or strip.

In one embodiment, the collagen biofabric is provided in a single sheet to be laid whole on a leg ulcer. In another embodiment, the collagen biofabric is provided as a mesh, netting or webbing that is capable of being spread out across the leg ulcer. In this embodiment, the collagen biofabric does not need to completely cover the surface area of the leg ulcer, but facilitates ingrowth of epithelial tissue along, and adjacent to, the collagen biofabric. Such a mesh, netting or webbing may be provided, in one embodiment, as a sheet of collagen biofabric containing a plurality of cuts enabling the end user to spread the sheet out into a netting, webbing or mesh. Such a mesh, netting or webbing may be made from a sheet of collagen biofabric by, for example, stamping, cutting or slicing, either manually or using a machine. Preferably, the stamping, cutting or slicing is performed under sterile conditions.

The collagen biofabric useful in the treatment methods of the invention may be provided to the end user either dry, or pre-wetted in a suitable physiologically-compatible, medically-useful liquid, such as a saline solution. In one embodiment, the solution comprises one or more bioactive compounds, as described in Section 4.2.2, above, without limitation. Preferably, said bioactive compound is disposed onto or within the collagen biofabric such that the majority of the bioactive compound contacts the leg ulcer during the time the collagen biofabric contacts the leg ulcer.

In another embodiment, the collagen biofabric is layered onto a support. Such a support may be non-natural, such as a plastic sheet or film, or a cloth woven of non-natural fibers, or may be natural, such as a cloth woven of natural fibers, or a non-collagen biofabric dermal replacement. In one embodiment, the support is a bandage; in this embodiment, the bandage and the collagen biofabric form a layered wound covering, with the bandage holding the collagen biofabric against the leg ulcer. In another embodiment, a sheet of collagen biofabric comprises a compound or material that is able to absorb excess wound exudates. In a specific embodiment, the compound or material is a collagen gel. In a more specific embodiment, said collagen gel is disposed on the fetal side of the collagen biofabric. In another more specific embodiment, said collagen gel is disposed on the maternal side of the collagen biofabric. In another more specific embodiment, said collagen gel is disposed on both sides of the collagen biofabric.

4.2.4 Method of Making Collagen Biofabric

Collagen biofabric, made from amniotic membrane, chorionic membrane, or both, may be produced by any means that preserves the biochemical and structural characteristics of the membrane's components—chiefly collagen, elastin, laminin, and fibronectin. A preferred material is the collagen biofabric described in, and produced according to the methods disclosed in, United States Application Publication No. U.S. 2004/0048796 A1, "Collagen Biofabric and Methods of Preparation and Use Therefor" by Hariri, which is hereby incorporated herein in its entirety.

Preferably, the collagen biofabric used to treat a leg ulcer is from a human placenta for use in human subjects, though the collagen biofabric may be made from amniotic membrane from a non-human mammal. Where the collagen biofabric is to be used in a non-human animal, it is preferred that the collagen biofabric be derived from a placenta from that species of animal In a preferred embodiment, the placenta for use in the methods of the invention is taken as soon as possible after delivery of the newborn. The placenta may be used immediately, or may be stored for 2-5 days from the time of delivery prior to any further treatment. The placenta is typically exsanguinated, that is, drained of the cord blood remaining after birth. Preferably, the expectant mother is screened prior to the time of birth, using standard techniques known to one skilled in the art, for communicable diseases including but not limited to, HIV, HBV, HCV, HTLV, syphilis, CMV, and other viral pathogens known to contaminate placental tissue.

One exemplary method for preparing a collagen biofabric of the invention comprises the following steps:

Step I. The umbilical cord is separated from the placental disc; optionally, the amniotic membrane is separated from the chorionic membrane. In a preferred embodiment, the amniotic membrane is separated from the chorionic membrane prior to cutting the placental membrane. Following separation of the amniotic membrane from the chorionic membrane and placental disc, the umbilical cord stump is cut, e.g., with scissors, and detached from the placental disc. The amniotic membrane may then be stored in a sterile, preferably buffered, saline solution, such as 0.9% sterile NaCl solution. Preferably, the amniotic membrane is stored by refrigeration, at a temperature of at least 2° C.

Step II. The amniotic membrane is substantially decellularized; that is, substantially all cellular material and cellular debris (e.g., all visible cellular material and cellular debris) is removed. Any decellularizing process known to one skilled in the art may be used, however, generally the process used for decellularizing the amniotic membrane of the invention does not disrupt the native conformation of the proteins making up the biofabric. "Substantial decellularization" of the amniotic membrane preferably removes at least 90% of the cells, more preferably removes at least 95% of the cells, and most preferably removes at least 99% of the cells (e.g., fibroblasts, amniocytes and chorionocytes). The amniotic membranes decellularized in accordance with the methods of the invention are uniformly thin, with inherent thickness variations of between about 2 and about 150 microns in the dry state, smooth (as determined by touch) and clear in appearance. Decellularization may comprise physical scraping, for example, with a sterile cell scraper, in combination with rinsing with a sterile solution. The decellularization technique employed should not result in gross disruption of the anatomy of the amniotic membrane or alter the biomechanical properties of the amniotic membrane. Preferably, the decellularization of the amniotic membrane comprises use of a detergent-containing solution, such as nonionic detergents, Triton X-100, anionic detergents, sodium dodecyl sulfate, Any mild anionic detergent, i.e., a non-caustic detergent, with a pH of 6 to 8, and low foaming, can be used to decellularize the amniotic membrane. In a specific embodiment, 0.01-1% deoxycholic acid sodium salt monohydrate is used in the decellularization of the amniotic membrane.

It is highly preferable to limit the protease activity in preparation of the biofabric. Additives to the lysis, rinse and storage solutions such as metal ion chelators, for example 1,10-phenanthroline and ethylenediaminetetraacetic acid (EDTA), create an environment unfavorable to many proteolytic enzymes. Providing sub-optimal conditions for proteases such as collagenase, assists in protecting amniotic membrane components such as collagen from degradation during the cell lysis step. Suboptimal conditions for proteases may be achieved by formulating the hypotonic lysis solution to eliminate or limit the amount of calcium and zinc ions available in solution. Many proteases are active in the presence of calcium and zinc ions and lose much of their activity in calcium and zinc ion free environments. Preferably, the hypotonic lysis solution will be prepared selecting conditions of pH, reduced availability of calcium and zinc ions, presence of metal ion chelators and the use of proteolytic inhibitors specific for collagenase such that the solution will optimally lyse the native cells while protecting the underlying amniotic membrane from adverse proteolytic degradation. For example a hypotonic lysis solution may include a buffered solution of water, pH 5.5 to 8, preferably pH 7 to 8, free from calcium and zinc ions and including a metal ion chelator such as EDTA. Additionally, control of the temperature and time parameters during the treatment of the amniotic membrane with the hypotonic lysis solution may also be employed to limit the activity of proteases.

It is preferred that the decellularization treatment of the amniotic membrane also limits the generation of new immunological sites. Since enzymatic degradation of collagen is believed to lead to heightened immunogenicity, the invention encompasses treatment of the amniotic membrane with enzymes, e.g., nucleases, that are effective in inhibiting cellular metabolism, protein production and cell division, that minimize proteolysis of the compositions of the amniotic membrane thus preserving the underlying architecture of the amniotic membrane. Examples of nucleases that can be used in accordance with the methods of the invention are those effective in digestion of native cell DNA and RNA including both exonucleases and endonucleases. A non-limiting example of nucleases that can be used in accordance with the methods of the invention include exonucleases that inhibit cellular activity, e.g., DNase I (SIGMA Chemical Company, St. Louis, Mo.) and RNase A (SIGMA Chemical Company, St. Louis, Mo.) and endonucleases that inhibit cellular activity, e.g., EcoRI (SIGMA Chemical Company, St. Louis, Mo.) and HindIII (SIGMA Chemical Company, St. Louis, Mo.). It is preferable that the selected nucleases are applied in a physiological buffer solution which contains ions, e.g., magnesium, calcium, which are optimal for the activity of the nuclease. Preferably, the ionic concentration of the buffered solution, the treatment temperature and the length of treatment are selected by one skilled in the art by routine experimentation to assure the desired level of nuclease activity. The buffer is preferably hypotonic to promote access of the nucleases to cell interiors.

In another embodiment of Steps I and II, above, the placenta, after initial processing, is briefly rinsed in saline to remove blood from the placental surface. The placental disk is then immersed in a cold deoxycholic acid solution at a concentration of about 0.1% to about 10%, and, in a specific embodiment, about 0.1% to about 2.0%. The placenta is then incubated in this solution at between about 1° C. to about 8° C. for about 5 days to about 6 months. In specific embodiments, the placental disk is immersed, for example, for about 5 to about 15 days; about 5 to about 30 days, about 5 to about 60 days, or for up to about one year. Typically, the deoxycholic acid solution is replaced during incubation every 2-5 days. In another specific embodiment, the placental disk is immersed in a deoxycholic acid solution at a concentration of about 1% at a temperature of 0° C. to about 8° C. for about 5 days to about 15 days. This incubation serves two purposes. First, it allows time for serological tests to be performed on the placental material and blood, so that placentas failing to meet serological criteria are not processed further. Second, the longer incubation improves the removal of epithelial cells and fibroblasts, which allows for a significant reduction in the amount of time spent decellularizing the amnion by physically scraping. Typically, the scraping time is reduced from, e.g., about 40 minutes to about 20 minutes. The amniotic membrane is then dried as described below.

Step III. Following decellularization, the amniotic membrane is washed to assure removal of cellular debris which may include cellular proteins, cellular lipids, and cellular nucleic acids, as well as any extracellular debris such as extracellular soluble proteins, lipids and proteoglycans. The wash solution may be de-ionized water or an aqueous hypotonic buffer. Preferably, the amniotic membrane is gently agitated for 15-120 minutes in the detergent, e.g., on a rocking platform, to assist in the decellularization. The amniotic membrane may, after detergent decellularization, again be physically decellularized as described above; the physical and detergent decellularization steps may be repeated as necessary, as long as the integrity of the amniotic membrane is maintained, until no visible cellular material and cellular debris remain.

In certain embodiments, the amniotic membrane is dried immediately (i.e., within 30 minutes) after the decellularization and washing steps. Alternatively, when further processing is not done immediately, the amniotic membrane may be refrigerated, e.g., stored at a temperature of about 1° C. to about 20° C., preferably from about 2° C. to about 8° C., for up to 28 days prior to drying. When the decellularized amniotic membrane is stored for more than three days but less than 28 days, the sterile solution covering the amniotic membrane is preferably changed periodically, e.g., every 1-3 days.

In certain embodiments, when the amniotic membrane is not refrigerated after washing, the amniotic membrane is washed at least 3 times prior to proceeding to Step IV of the preparation. In other embodiments, when the amniotic membrane has been refrigerated and the sterile solution has been changed once, the amniotic membrane is washed at least twice prior to proceeding to Step IV of the preparation. In yet other embodiments, when the amniotic membrane has been refrigerated and the sterile solution has been changed twice or more, the amniotic membrane is washed at least once prior to proceeding to Step IV of the preparation.

Prior to proceeding to Step IV, it is preferred that all bacteriological and serological testing be assessed to ensure that all tests are negative.

Step IV. The final step in this embodiment of the method of collagen biofabric production comprises drying the decellularized amniotic membrane of the invention to produce the collagen biofabric. Any method of drying the amniotic membrane so as to produce a flat, dry sheet of collagen may be used. Preferably, however, the amniotic membrane is dried under vacuum.

In a specific embodiment, an exemplary method for drying the decellularized amniotic membrane of the invention comprises the following steps:

Assembly of the decellularized amniotic membrane for drying. The decellularized amniotic membrane is removed from the sterile solution, and the excess fluid is gently squeezed out. The decellularized amniotic membrane is then gently stretched until it is flat with the fetal side faced in a downward position, e.g., on a tray. The decellularized amniotic membrane is then flipped over so that fetal side is facing upwards, and placed on a drying frame, preferably a plastic mesh drying frame (e.g., Quick Count® Plastic Canvas, Uniek, Inc., Waunakee, Wis.). In other embodiments, the drying frame may be any autoclavable material, including but not limited to a stainless steel mesh. In a most preferred embodiment, about 0.5 centimeter of the amniotic membrane overlaps the edges of the drying frame. In certain embodiments, the overlapping amniotic membrane extending beyond the drying frame is wrapped over the top of the frame, e.g., using a clamp or a hemostat. Once the amniotic membrane is positioned on the drying frame, a sterile gauze is placed on the drying platform of a heat dryer (or gel-dryer) (e.g., Model 583, Bio-Rad Laboratories, 200 Alfred Nobel Drive, Hercules, Calif. 94547), so that an area slightly larger than the amniotic membrane resting on the plastic mesh drying frame is covered. Preferably, the total thickness of the gauze layer does not exceed the thickness of one folded 4×4 gauze. Any heat drying apparatus may be used that is suitable for drying sheet like material. The drying frame is placed on top of the gauze on the drying platform so that the edges of the plastic frame extend above beyond the gauze edges, preferably between 0.1-1.0 cm, more preferably 0.5-1.0 cm. In a most preferred embodiment, the drying frame having the amniotic membrane is placed on top of the sterile gauze with the fetal side of the amniotic membrane facing upward. In some embodiments, another plastic framing mesh is placed on top of the amniotic membrane. A view of the mesh frame and the membrane dried therein is shown in FIG. 4. In another embodiments, a sheet of thin plastic (e.g., SW 182, clear PVC, AEP Industries Inc., South Hackensack, N.J. 07606) or a biocompatible silicone is placed on top of the membrane covered mesh so that the sheet extends well beyond all of the edges. In this embodiment, the second mesh frame is not needed.

In an alternative embodiment, the amniotic membrane is placed one or more sterile sheets of Tyvek® material (e.g., a sheet of Tyvek® for medical packaging, Dupont Tyvek®, P.O. Box 80705, Wilmington, Del. 19880-0705), optionally, with one sheet of Tyvek® on top of the membrane (prior to placing the plastic film). This alternate process will produce a smoother version of the biofabric (i.e., without the pattern of differential fiber compression regions along and perpendicular to the axis of the material), which may be advantageous for certain applications, such as for example for use as a matrix for expansion of cells.

Drying the amniotic membrane. In a preferred embodiment, the invention encompasses heat drying the amniotic membrane of the invention under vacuum. While the drying under vacuum may be accomplished at any temperature from about 0° C. to about 60° C., the amniotic membrane is preferably dried at between about 35° C. and about 50° C., and most preferably at about 50° C. It should be noted that some degradation of the collagen is to be expected at temperatures above 50° C. The drying temperature is preferably set and verified using a calibrated digital thermometer using an extended probe. Preferably, the vacuum pressure is set to about −22 inches of Hg. The drying step is continued until the collagen matrix of the amniotic membrane is substantially dry, that is, contains less than 20% water by weight, and preferably, about 3-12% water by weight as determined for example by a moisture analyzer. To accomplish this, the amniotic membrane may be heat-vacuum dried, e.g., for approximately 60 minutes to achieve a dehydrated amniotic membrane. In some embodiments, the amniotic membrane is dried for about 30 minutes to 2 hours, preferably about 60 minutes. Although not intending to be bound by any mechanism of action, it is believed that the low heat setting coupled with vacuum pressure allows the amniotic membrane to achieve the dehydrated state without denaturing the collagen.

After completion of the drying process in accordance with the invention, the amniotic membrane is cooled down for approximately two minutes with the vacuum pump running.

Packaging and Storing of the Amniotic Membrane. Once the amniotic membrane is dried, the membrane is gently lifted off the drying frame. "Lifting off" the membrane may comprise the following steps: while the pump is still running, the plastic film is gently removed from the amniotic membrane starting at the corner, while holding the amniotic membrane down; the frame with the amniotic membrane is lifted off the drying platform and placed on a cutting board with the amniotic membrane side facing upward; an incision is made, cutting along the edge 1-2 mm away from the edge of the frame;

the amniotic membrane is then peeled off the frame. Preferably, handling of the amniotic membrane at this stage is done with sterile gloves.

The amniotic membrane is placed in a sterile container, e.g., peel pouch, and is sealed. The biofabric produced in accordance with the methods of the invention may be stored at room temperature for an extended period of time as described supra.

In alternative embodiments, the invention provides a method of preparing a collagen biofabric comprising a chorionic membrane, or both a chorionic membrane and an amniotic membrane. It is expected that the methods described above would be applicable to the method of preparing a biofabric comprising a chorionic membrane, or both a chorionic membrane and an amniotic membrane. In one embodiment, the invention encompasses the use of a collagen biofabric prepared by providing a placenta comprising an amniotic membrane and a chorionic membrane; separating the amniotic membrane from the chorionic membrane; and decellularizing the chorionic membrane. In a specific embodiment, the method further entails washing and drying the decellularized chorionic membrane. In another embodiment, the invention encompasses the use of a collagen biofabric prepared by providing a placenta comprising an amniotic membrane and a chorionic membrane, and decellularizing the amniotic and chorionic membranes. In a specific embodiment, the method further entails washing and drying the decellularized amniotic and chorionic membranes.

4.2.5 Storage And Handling Of Collagen Biofabric

Dehydrated collagen biofabric may be stored, e.g., as dehydrated sheets, at room temperature (e.g., 25° C.) prior to use. In certain embodiments, the collagen biofabric can be stored at a temperature of at least 10° C., at least 15° C., at least 20° C., at least 25° C., or at least 29° C. Preferably, collagen biofabric, in dehydrated form, is not refrigerated. In some embodiments, the collagen biofabric may be refrigerated at a temperature of about 2° C. to about 8° C. The biofabric produced according to the methods of the invention can be stored at any of the specified temperatures for 12 months or more with no alteration in biochemical or structural integrity (e.g., no degradation), without any alteration of the biochemical or biophysical properties of the collagen biofabric. The biofabric can be stored for several years with no alteration in biochemical or structural integrity (e.g., no degradation), without any alteration of the biochemical or biophysical properties of the collagen biofabric. The biofabric may be stored in any container suitable for long-term storage. Preferably, the collagen biofabric of the invention is stored in a sterile double peel-pouch package.

The collagen biofabric may be hydrated prior to use. The collagen biofabric can be rehydrated using, e.g., a sterile physiological buffer. In a specific embodiment, the sterile saline solution is a 0.9% NaCl solution. In some embodiments the sterile saline solution is buffered. In certain embodiments, the hydration of the collagen biofabric of the invention requires at least 2 minutes, at least 5 minutes, at least 10 minutes, at least 15 minutes, or at least 20 minutes. In a preferred embodiment, the hydration of the collagen biofabric of the invention is complete within 5 minutes. In yet another preferred embodiment, the hydration of the collagen biofabric of the invention is complete within 10 minutes. In yet another embodiment, the hydration of the collagen biofabric of the invention takes no more than 10 minutes. Once hydrated, the collagen biofabric may be maintained in solution, e.g., sterile 0.9% NaCl solution, for up to six months, with a change of solution, e.g., every three days.

4.2.6 Sterilization

Sterilization of the biofabric may be accomplished by any medically-appropriate means, preferably means that do not significantly alter the tertiary and quaternary structure of the amniotic membrane proteins. Sterilization may be accomplished, for example, using gas, e.g., ethylene dioxide. Sterilization may be accomplished using radiation, for example, gamma radiation, and is preferably done by electron beam irradiation using methods known to one skilled in the art, e.g., Gorham, D. Byrom (ed.), 1991, Biomaterials, Stockton Press, New York, 55-122. Any dose of radiation sufficient to kill at least 99.9% of bacteria or other potentially contaminating organisms is within the scope of the invention. In a preferred embodiment, a dose of at least 18-25 kGy is used to achieve the terminal sterilization of the biofabric.

4.2.7 Laminates

The collagen biofabric may be laminated to provide greater stiffness and durability during the healing process (typically about three months). The collagen biofabric may be laminated as follows.

Collagen biofabric is typically laminated by stacking 2 or more layers of collagen biofabric one atop the other and sealing or drying. The collagen biofabric may be laminated either dry or after rehydration. Alternatively, two or more layers of, e.g., amniotic membrane may be laminated prior to initial drying after cell removal, e.g., via a cell scraping step (see Examples, below). If laminated prior to the initial drying, 2 or more collagen biofabric layers may be stacked one atop the other and subsequently dried, using, for example, a freeze-drying process, or drying under moderate heat with or without vacuum. The heat applied preferably is not so intense as to cause breakdown or decomposition of the protein components, especially the collagen, of the collagen biofabric. Typically, the heat applied is no more than about 70° C., preferably no more than about 60° C., and, more preferably, is approximately 50° C. Lamination time varies with, e.g., the number of layers being laminated, but typically takes 1-2 hours at 50° C. for the size pieces of collagen biofabric used for tympanic membrane repair. Preferably, the collagen biofabric laminate comprises 2-6 layers of collagen biofabric. In one preferred embodiment, the collagen biofabric laminate has two layers and is approximately 50 micrometers in thickness. In another embodiment, the collagen biofabric laminate has two layers and has a thickness of about 20-60 microns. Preferably, each of the layers is from the same collagen biofabric lot, that is, the same placenta.

The collagen biofabric may also be laminated using an adhesive applied between 2 or more layers of collagen biofabric or amniotic membrane. Such an adhesive is preferably appropriate for medical applications, and can comprise a natural biological adhesive, for example fibrin glue, a synthetic adhesive, or combinations thereof. The adhesive may further be chemically converted from precursors during the lamination process.

4.2.8 Stem Cells

The collagen biofabric used in the treatment methods described herein may also comprise stem or progenitor cells. Preferably, the collagen biofabric comprises mesenchymal or mesenchymal-like stem cells, for example, those described in U.S. Pat. Nos. 5,486,359, 6,261,549 and 6,387,367, or placenta-derived stem cells such as those described in U.S. Pat. No. 7,045,148 or in U.S. Application Publication Nos. 2003/0032179 and 2003/0180269. However, the collagen biofabric may comprise stem or progenitor cells, preferably mammalian stem or progenitor cells, from any tissue source. The collagen biofabric may comprise embryonic stem cells or embryonic germ cells.

The combination of collagen biofabric and stem or progenitor cells may be accomplished prior to or during application of the collagen biofabric to the leg ulcer. For example, a sheet or piece of collagen biofabric may be prepared immediately prior to application on the venous leg ulcer by disposing on the surface of the collagen biofabric a solution of stem or progenitor cells and allowing the stem or progenitor cells sufficient time to attach to the collagen biofabric. The stem or progenitor cells, alternately, may be disposed onto the surface of the collagen biofabric 30 minutes, 1, 2, 3, 4, 5, 6, 7, 8, 9, 10, 12, 14, 16, 18, 20, 22, 24 or more hours prior to application of the collagen biofabric onto the leg ulcer. The number of stem or progenitor cells disposed onto the surface of the collagen biofabric may vary, but may be at least $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$; or may be no more than $1\times10^6$, $3\times10^6$, $1\times10^7$, $3\times10^7$, $1\times10^8$, $3\times10^8$, $1\times10^9$, $3\times10^9$, $1\times10^{10}$, $3\times10^{10}$, $1\times10^{11}$, $3\times10^{11}$, or $1\times10^{12}$ stem or progenitor cells. Alternatively, in another embodiment, the stem or progenitor cells, in the number indicated above, may be disposed on the surface of the collagen biofabric after the collagen biofabric has been applied to the leg ulcer. In another embodiment, the stem cells are applied directly to the leg ulcer in any of the amounts indicated above, and the leg ulcer is covered with the collagen biofabric. In a more specific embodiment, the stem cells are applied in a physiologically-acceptable liquid, such as a saline solution, or embedded in a physiologically-acceptable gel, such as a hydrogel, in which the stem or progenitor cells may be maintained and migrate through. The stem cells, prior to or after contacting with the leg ulcer, may be contacted with one or more differentiation-modulating agents, for example, the differentiation-modulating agents described in U.S. Application Publication Nos. 2003/0235909, 2004/0028660, or International Application Publication No. WO 03/087333. Methods of differentiating stem cells to, for example, epidermal, mesodermal, and other cell types are known in the art, and are described, e.g., in U.S. Application Publication No. 2004/0028660.

4.3 Kits

Collagen biofabric, useful for the methods of leg ulcer treatment of the present invention may be provided in a wrapping or container as part of a kit for the facilitation of the treatment of leg ulcers. In a specific embodiment, the collagen biofabric is provided an a sterile double-peel package. In a more specific embodiment, the collagen biofabric is about 6×8 cm. The kit may comprise one or more pieces of collagen biofabric and any other medical device, disposable or drug that would facilitate treatment of a leg ulcer. Preferably, each piece of the collagen biofabric in the kit is provided as a single sheet or patch in a sterile container or wrapping separate from the remainder of kit contents. In another embodiment, the kit comprises two or more pieces of collagen biofabric, separately wrapped or contained. In another embodiment, said kit comprises a support for the collagen biofabric. In specific embodiments, the support may be a natural or a synthetic material. In other specific embodiments, said support is a plastic film, plastic sheet, or a stretchable plastic wrap. In another embodiment, said kit comprises one or more disposables. In a specific embodiment, said disposables are bandages, means for sterilizing the skin surrounding a leg ulcer, swabs, gloves, or sterile sheets. In another embodiment, said kit comprises an anti-infective agent. In a specific embodiment, the anti-infective agent is an antibiotic ointment, cream, or spray. In another embodiment, said kit comprises a piece of collagen biofabric and one or more wound healing agents. In a specific embodiment, said wound healing agent is PDGF, TGF, hyaluronic acid, fibrin, or fibronectin. In another embodiment, said kit comprises collagen biofabric and a means for applying compression to the lower leg. In a specific embodiment, of any of the kits above, the kit comprises an instruction sheet suitable for use by a non-medical end user; an instruction sheet suitable for use by an end user in a medical profession; or a materials safety data sheet; or a combination thereof.

5. EXAMPLES 5.1 Example 1

Method of Making Collagen Biofabric

Materials

The following materials were used in preparation of the collagen biofabric.

Materials/Equipment
Copy of Delivery Record
Copy of Material/Family Health History/Informed Consent
Source Bar Code Label (Donor ID number)
Collection # (A sequential number is assigned to incoming material)
Tissue Processing Record (Document ID #ANT-19F); a detailed record of processing of each lot number is maintained
Human Placenta (less than 48 hours old at the start of processing)
Sterile Surgical Clamps/Hemostats
Sterile Scissors
Sterile Scalpels
Sterile Steri-Wrap sheets
Sterile Cell Scraper (Nalgene NUNC Int. R0896)
Sterile Gauze (non-sterile PSS 4416, sterilized)
Sterile Rinsing Stainless Steel Trays
Disinfected Processing Stainless Steel Trays
Disinfected Plastic Bin
Sterile 0.9% NaCl Solution (Baxter 2F7124)
Sterile Water (Milli Q plus 09195 or Baxter 2F7113)
Sterile Specimen Containers (VWR 15704-014)
Personal Protective Equipment (including sterile and non-sterile gloves)
Certified Clean Room
Previously Prepared Decellularizing Solution (D-cell); 0.01-1% deoxycholic acid sodium monohydrate
Disinfected Bin
Rocking Platform (VWR Model 100)
Timer (VWR 21376890)
Disinfected Plastic Frame Mesh
PVC Wrap Film
Vacuum Pump (Schuco-Vac 5711-130)
Gel Dryer (i.e., heat dryer; BioRad Model 583)
Disinfected Stainless Steel Cutting Board
Pouches for Packaging
Sterile Stainless Steel Ruler (General Tools MFG. Co 1201)
Traceable Digital Thermometer (Model 61161-364, Control Company)
Accu-Seal Automatic Sealer (Accu-Seal, Model 630-1B6)

The expectant mother was screened at the time of birth for communicable diseases such as HIV, HBV, HCV, HTLV, syphilis, CMV and other viral and bacterial pathogens that could contaminate the placental tissues being collected. Only tissues collected from donors whose mothers tested negative or non-reactive to the above-mentioned pathogens were used to produce the collagen biofabric.

Following normal birth, the placenta, umbilical cord and umbilical cord blood were spontaneously expelled from the contracting uterus. The placenta, umbilical cord, and umbilical cord blood were collected following birth. The materials were transported to the laboratory where they were processed under aseptic conditions in a Clean room having a HEPA filtration system, which was turned on at least one hour prior to processing. Gloves (sterile or non-sterile, as appropriate) were worn at all times while handling the product. All unused (waste) segments of the amnion/chorion and contaminated liquids generated during tissue processing were disposed of as soon as feasible.

Step I.

A sterile field was set up with sterile Steri-Wrap sheets and the following instruments and accessories for processing were placed on it.
  sterile tray pack
  sterile Cell Scraper
  sterile scalpel
  disinfected processing tray Sterile pack ID # was recorded in the Processing Record.

The placenta was removed from the transport container and placed onto the disinfected stainless steel tray. Using surgical clamps and scissors, the umbilical cord was cut off approximately 2 inches from the placental disc. The umbilical cord was placed into a separate sterile container for further processing. The container was labeled with Tissue ID Bar Code; and the material and storage solution(s) present (e.g., type of media) were identified. In some cases, the umbilical cord was discarded if not requested for other projects.

Starting from the edge of the placental membrane, the amnion was separated from the chorion using blunt dissection with fingers. This was done prior to cutting the membrane.

After the amnion was separated from the entire surface of the chorion and placental disc, the amniotic membrane was cut around the umbilical cord stump with scissors and detached from the placental disc. In some instances, if the separation of the amnion and chorion was not possible without tearing the tissue, the amnion and chorion were cut from the placental disc as one piece and then peeled apart.

The chorion was placed into a separate specimen container to be utilized for other projects. The container was labeled with the Tissue ID Bar Code, the material and storage solution(s) present (e.g., type of media) were identified, initialed and dated.

If any piece of amnion was still attached to the placental disc it was peeled from the disc and cutting off around the umbilical cord with scissors. The placenta was placed back into the transport container to be utilized for other projects.

The appropriate data was recorded in the Tissue Processing Record.

The amniotic membrane was kept in the tray with sterile 0.9% NaCl solution. Preferably, the amniotic membrane is stored by refrigeration for a maximum of 72 hours from the time of delivery prior to the next step in the process.

Step II.

The amniotic membrane was removed from the specimen container one piece at a time and placed onto the disinfected stainless steel tray. Other pieces were placed into a separate sterile stainless steel tray filled with sterile water until they were ready to be cleaned. Extra pieces of amnion from the processing tray were removed and placed in a separate rinsing stainless steel tray filled with sterile water.

The amniotic membrane was rinsed with sterile water if grossly contaminated with blood maternal or fetal fluids/materials changing sterile water as needed.

The amniotic membrane was placed on the processing tray with the maternal side facing upward. Using a sterile Cell Scraper, as much as possible of visible contamination and cellular material from the maternal side of the amnion was carefully removed. (Note: minimal pressure should be applied for this step to prevent tearing the membrane). Sterile water was used to aid in the removal of cells and cellular debris. The amniotic membrane was further rinsed with sterile water in the separate sterile stainless steel rinsing tray.

The amniotic membrane was turned over so that the fetal side was facing upward and placed back on the processing tray and rinsed with sterile water. Visible cellular material and debris using the Cell Scraper was gently removed (Note: minimal pressure should be applied for this step to prevent tearing the membrane). Sterile water was used to aid in the removal of cells and cellular debris.

The amniotic membrane was rinsed with sterile water in between cleaning rounds in separate sterile rinsing trays. The tissue was cleaned as many times (cleaning rounds) as necessary to remove most if not all of visible cellular material and debris from both sides of the membrane. The sterile water was changed in the rinsing trays in between rinses.

The processing tray was rinsed with sterile water after each cleaning round.

All other pieces of amnion were processed in the same manner and placed into the same container. Tissue Id Bar Code was affixed, the material and storage solution(s) present (e.g., type of media) were identified, initials date were added.

The appropriate information and the date were recorded in the Tissue Processing Record.

Step III.

The amniotic membrane was removed from the rinsing tray, (or from storage container) excess fluid was gently squeezed out with fingers and the membrane was placed into the sterile specimen container. The container was filled up to the 150 ml mark with D-cell solution ensuring that all of the amniotic membrane was covered and the container was closed.

The container was placed in the bin on the rocking platform. The rocking platform was turned on and the membrane was agitated in D-cell solution for a minimum of 15 minutes and a maximum of 120 minutes at Setting #6.

A new sterile field was set up with new sterile instruments and disinfected tray in a same manner as in the Step I. Sterile pack ID # was recorded in the Processing Record.

After agitation was completed, the rocking platform was turned off and the membrane was removed from the container. The membrane was placed into a new sterile stainless steel processing tray. Sterile 0.9% NaCl solution was added to cover the bottom of the tray.

Using a new sterile Cell Scraper, residual D-cell and cellular material (if any) was removed from both sides of the tissue. This step was repeated as many times as needed to remove as much as possible of visible residual cellular material from the entire surface on both sides. The membrane was rinsed with sterile 0.9% NaCl solution in a separate rinsing tray in between cleaning rounds. The sterile 0.9% NaCl solution was changed in the rinsing trays in between rinses.

After the last cleaning round was completed, the membrane was rinsed with sterile 0.9% NaCl solution and placed into the new sterile specimen container filled with sterile 0.9% NaCl solution.

All remaining pieces of amniotic membrane were processed in exactly the same manner.

When all amniotic membrane pieces were processed and in the container with the sterile 0.9% NaCl solution, the container was placed in the bin on the rocking platform to agitate for a minimum of 5 minutes at setting #6. After agitation was completed, the membrane was removed from the specimen container, the sterile 0.9% NaCl solution was changed in the container and the membrane was placed back into the specimen container.

The specimen container was labeled with Tissue ID Bar Code and Quarantine label. The material and storage solution(s) present (e.g., type of media) were identified, initialed and dated. The specimen container was placed into a clean zip-lock bag and placed in the refrigerator (2-8° C.).

All appropriate data was recorded in the Tissue Processing Record.

When serology results became available, the appropriate label (Serology Negative or For Research Use Only) was placed on the top of the Quarantine label and those containers were segregated from Quarantined ones.

Step IV.

Before proceeding with Step IV, the Tissue Status Review was checked to make sure all applicable test results were negative.

A sterile field was set up with sterile Steri-Wrap sheet and all sterile and disinfected instruments and accessories were set up in the same manner as in Steps II and III.

The membrane was removed from the refrigerator and placed into a new sterile stainless steel processing tray. Sterile 0.9% NaCl solution was added to cover the bottom of the tray.

All visible cellular material and debris (if any) was gently removed using a new sterile Cell Scraper (Note: minimal pressure should be applied for this step to prevent tearing the membrane). Sterile 0.9% NaCl solution was used to aid in removal of the cells and debris.

The membrane was rinsed in the separate sterile stainless steel rinsing tray filled with the sterile 0.9% NaCl Solution. 0.9% NaCl Solution was changed in between cleaning rounds. The membrane was placed into a new sterile specimen container, the container was filled with fresh sterile 0.9% NaCl solution and placed on the rocking platform for agitation for a minimum of 5 minutes at Setting #6.

The previous step was repeated 3 times and the sterile 0.9% NaCl solution was changed in between each agitation. Appropriate data was recorded in the Tissue Processing Record.

The membrane was removed from the specimen container one piece at a time, excess fluid was gently squeezed out with fingers and the membrane was placed onto a sterile processing tray. The membrane was gently stretched until flat; ensuring it was fetal side down.

The frame was prepared by cutting the disinfected plastic sheet with sterile scissors. The size of the frame should be approximately 0.5 cm smaller in each direction than the membrane segment. The frame was rinsed in the rinsing tray filled with sterile 0.9% NaCl solution.

The frame was placed on the slightly stretched membrane surface and pressed on it gently. It is imperative that the smooth side of the plastic frame faces the tissue.

Using a scalpel, the membrane was cut around the frame leaving approximately 0.5 cm extending beyond frame edges. The excess membrane was placed back into the specimen container The membrane edges that are extended beyond the frame were wrapped over the edges of the frame using clamps or tweezers and put aside on the same tray.

The next piece of membrane was processed in the same manner. It is preferred that the total area to be dried does not exceed 300 cm$^2$ per heat dryer. While 'framing out' the piece of membrane, it is preferred that the non-framed pieces remain in the container in sterile 0.9% NaCl solution.

The drying temperatures of dryers were set and verified using a calibrated digital thermometer with extended probe. The drying temperature was set at 50° C. The data was recorded in the Tissue Processing Record.

The vacuum pump was turned on.

A sterile gauze was placed on the drying platform of the heat dryer, covering an area slightly larger than the area of the framed membrane. It is important to make sure that the total thickness of the gauze layer does not exceed thickness of one folded 4×4 gauze.

One sheet of plastic framing mesh was placed on top of the gauze. The plastic mesh edges should extend approximately 0.5-1.0 cm beyond gauze edges.

The framed membrane was gently lifted and placed on the heat dryer platform on top of the plastic mesh with the membrane side facing upward. This was repeated until the maximum amount of membrane (without exceeding 300 cm$^2$) was on the heat dryer platform. (NOTE: fetal side of the amnion is facing up).

A piece of PVC wrap film was cut large enough to cover the entire drying platform of the heat dryer plus an extra foot.

With the vacuum pump running, the entire drying platform of the heat dryer was gently covered with the plastic film leaving ½ foot extending beyond drying platform edges on both sides. Care was taken that the film pull tightly against the membrane and frame sheet (i.e., it is "sucked in" by the vacuum) and that there were no air leaks and no wrinkles over the tissue area). The lid was subsequently closed.

The vacuum pump was set to approximately −22 inches Hg of vacuum. The pump gage was recorded after 2-3 min of drying cycle. The membrane was heat vacuum dried for approximately 60 minutes. Approximately 15-30 minutes into the drying process, the sterile gauze layer was replaced in the heat dryer with a new one. The total thickness of the gauze layer must not exceed thickness of one folded 4×4 gauze.

After the change, care was taken so that the plastic film pulled tightly against the membrane and the frame sheet and there were no air leaks and no wrinkles over the membrane area.

The integrity of the vacuum seal was periodically checked by checking the pump pressure manometer. After completion of the drying process, the heat dryer was opened and the membrane was cooled down for approximately two minutes with the pump running.

A new sterile field was set up with sterile Steri-wrap and disinfected stainless steel cutting board underneath it. As this point sterile gloves were used. With the pump still running, the plastic film was gently removed from the membrane sheet starting at the corner and holding the membrane sheet down with a gloved hand. The frame was gently lifted with the membrane off the drying platform and placed on the sterile field on the top of the disinfected stainless steel cutting board with the membrane side facing upward. Using a scalpel, the membrane sheet was cut through making an incision along the edge 1-2 mm away from the edge of the frame. The membrane was held in place with a gloved (sterile glove) hand. Gently the membrane sheet was lifted off of the frame by peeling it off slowly and then placed on the sterile field on the cutting board.

Using scalpel or sharp scissors, the membrane sheet was cut into segments of specified size. All pieces were cut and secured on the sterile field before packaging. A single piece of membrane was placed inside the inner peel-pouch package with one hand (sterile) while holding the pouch with another hand (non-sterile). Care was taken not to touch pouches with 'sterile' hand. After all pieces were inside the inner pouches they were sealed. A label was affixed with the appropriate information (e.g., Part #, Lot #, etc.) in the designated area on the outside of the pouch. All pieces of membrane were processed in the same manner. The labeled and sealed peel-pouch packages were placed in the waterproof zip-lock bag for storage until they were ready to be shipped to the sterilization facility or distributor. All appropriate data were recorded on the Tissue Processing Record.

5.2 Example 2

Alternative Method of Making Collagen Biofabric

A placenta is prepared substantially as described in Step I of Example 1 using the Materials in that Example. An expectant mother is screened at the time of birth for communicable diseases such as HIV, HBV, HCV, HTLV, syphilis, CMV and other viral and bacterial pathogens that could contaminate the placental tissues being collected. Only tissues collected from donors whose mothers tested negative or non-reactive to the above-mentioned pathogens are used to produce the collagen biofabric.

A sterile field is set up with sterile Steri-Wrap sheets and the following instruments and accessories for processing were placed on it: sterile tray pack; rinsing tray, stainless steel cup, clamp/hemostats, tweezers, scissors, gauze.

The placenta is removed from the transport container and placed onto a disinfected stainless steel tray. Using surgical clamps and scissors, the umbilical cord is cut off approximately 2 inches from the placental disc.

Starting from the edge of the placental membrane, the amnion is separated from the chorion using blunt dissection with fingers. This is done prior to cutting the membrane. After the amnion is separated from the entire surface of the chorion and placental disc, the amniotic membrane is cut around the umbilical cord stump with scissors and detached from the placental disc. In some instances, if the separation of the amnion and chorion is not possible without tearing the tissue, the amnion and chorion is cut from the placental disc as one piece and then peeled apart.

The appropriate data is recorded in the Tissue Processing Record.

The amniotic membrane is rinsed with sterile 0.9% NaCl solution to remove blood and fetal fluid or materials. The saline solution is replaced as necessary during this rinse.

The amnion is then placed in a 0.9% saline, 1.0% deoxycholic acid solution in a specimen container and refrigerated at 2-8° C. for up to 15 days, with changes of the solution every 3-5 days. During or at the end of incubation, the serological tests noted above are evaluated. If the tests indicate contamination with one or more pathogens, the amnion is rejected and processed no further. Tissue indicated as derived from a CMV-positive donor, however, is still suitable for production of biofabric.

Once the incubation is complete, the amnion is removed from the specimen container, placed in a sterile tray and rinsed three times with 0.9% NaCl solution to reduce the deoxycholic acid from the tissue. With the amnion placed maternal side up, the amnion is gently scraped with a cell scraper to remove as much cellular material as possible. Additional saline is added as needed to aid in the removal of cells and cellular debris. This step is repeated for the fetal side of the amnion. Scraping is followed by rinsing, and is repeated, both sides, as many times as necessary to remove cells and cellular material. The scraped amnion is rinsed by placing the amnion in 0.9% saline solution a separate container on a rocking platform for 5-120 minutes at setting #6. The saline solution is replaced, and the rocking rinse is repeated.

After rinsing is complete, the amnion is optionally stored in a zip-lock bag in a refrigerator.

The scraped amnion is then placed fetal side down onto a sterile processing tray. The amnion is gently massaged by hand to remove excess liquid, and to flatten the membrane. A sterile plastic sheet is cut so that its dimensions are approximately 0.5 cm smaller in each direction than the flat amnion. This plastic sheet is briefly rinsed in 0.9% NaCl solution. The plastic sheet is placed, smooth side down, on the flattened amnion, leaving a margin of uncovered amnion. A scalpel is used to trim the amnion, leaving approximately 0.5 cm extending beyond the sheet edges. These extending amnion edges are wrapped back over the plastic sheet. The total tissue area to be dried does not exceed 300 cm$^2$ for a standard vacuum heat dryer.

A sheet of sterile gauze is placed in a vacuum heat dryer. A thin plastic mesh is placed on the gauze so that approximately 0.5-10.0 cm extends beyond the edges of the gauze. The amnion and plastic sheet are then placed into the vacuum heat dryer on top of the mesh, tissue side up, and the amnion is covered with a sheet of PVC wrap film. The dryer is set at 50° C., and the temperature is checked periodically to ensure maintenance of 50° C.±1° C. The vacuum pump is then turned on and set to approximately −22 inches Hg vacuum. Drying is allowed to proceed for 60 minutes.

The dried amnion is then stored in a sealed plastic container for further use.

5.3 Example 3

Collagen Biofabric Laminate

The collagen biofabric produced by the methods described in Example 1, above, was laminated as follows. "Dry" collagen biofabric was produced by the procedure outlined in Example 1, above, then rehydrated and laminated. "Wet" collagen biofabric was prepared up to Step III of Example 1 (that is up to the point of vacuum drying), then laminated. After mounting frames were cut and the "dry" biofabric was rehydrated, both types of biofabric were mounted by placing the fetal side down, placing the mounting frame on top of the tissue, and cutting the tissue, leaving about 1 cm edge around the frame. The 1 cm edge was folded over the edge of the frame using a cell scraper. These steps were repeated for adding additional pieces of collagen biofabric. The laminated biofabric was then placed in a gel dryer and dried to substantial dryness (<20% water content by weight). Laminates were then cut to 2×6 cm samples.

Separate lots of the laminated collagen biofabric were evaluated as follows. Dimensions of dry (DT) and wet (WT) laminated collagen biofabric were determined for laminates containing 2, 3, 5 or 8 layers, as shown in Table 1:

TABLE 1

|  | Thickness (μm) | Length (mm) | Width (mm) | Weight (mg) |
|---|---|---|---|---|
| DT2 | 29 ± 12 | 20.0 ± 0.3 | 5.2 ± 0.1 | 0.87 ± 0.02 |
| DT3 | 32 ± 2 | 20.5 ± 0.1 | 5.2 ± 0.2 | 1.26 ± 0.11 |
| WT2 | 20 ± 15 | 20.2 ± 0.2 | 5.0 ± 0.3 | 0.93 ± 0.17 |
| WT3 | 15 ± 5 | 19.6 ± 0.1 | 5.1 ± 0.3 | 0.9 ± 0.04 |
| WT5 | 31 ± 5 | 19.8 ± 0.4 | 5.3 ± 0.1 | 2.06 ± 0.2 |
| WT8 | 115 ± 26 | 20.3 ± 0.2 | 5.1 ± 0.4 | 4.92 ± 0.56 |

Specimens showed no signs of delamination over the first two days post-lamination, when kept under dry conditions at room temperature. The laminated collagen biofabric additionally showed no signs of delamination when kept in stirred 0.9% saline, room temperature, for ten days.

Larger laminated collagen biofabric specimens were tested for laminate durability and resistance to delamination. 1×2 cm specimens from the list listed above (i.e., DT2, DT3, WT2, WT3, WT5 and WT8) were placed in Petri dishes in 5 ml phosphate buffered saline. The specimens were left on an orbital shaker for approximately 24 hours at 95 RPM. No delamination of the specimens was observed, either during shaking or thereafter during simple handling.

5.4 Example 4

Methods of Treatment

A patient presents with a venous leg ulcer on the inside ankle area of the right leg. The leg ulcer is evaluated for infection. The leg ulcer is debrided after administration of a local anesthetic. The leg ulcer is measured, and a small sheet of collagen biofabric is selected that will completely cover the leg ulcer. The collagen biofabric is placed on the leg ulcer and gently pressed into the leg ulcer so that the collagen biofabric contacts substantially all of the ulcerated tissue with no or only small air pockets. The collagen biofabric is allowed to adhere to the leg ulcer by adsorption to the ulcer. The collagen biofabric is then covered with a dressing to prevent disturbance of the leg ulcer. A second sheet of collagen biofabric is placed on the healing wound 4-5 weeks after the first application, in the same manner as the first application. If necessary, a third application is performed at the 8-9 week mark, and every 3-4 thereafter as needed. The leg ulcer is evaluated every 3-4 weeks during the wound healing process.

A second patient presents with a venous leg ulcer on the inside ankle area of the right leg. The leg ulcer is evaluated for infection. The leg ulcer is debrided after administration of a local anesthetic. The leg ulcer is measured, and a small sheet of collagen biofabric is selected that will completely cover the leg ulcer. The collagen biofabric is placed on the leg ulcer and gently pressed into the leg ulcer so that the collagen biofabric contacts substantially all of the ulcerated tissue with no or only small air pockets. The collagen biofabric is allowed to adhere to the leg ulcer by adsorption to the ulcer. The collagen biofabric, and the lower leg, is then covered with a compression bandage. The compression bandage is maintained on the leg for the duration of the healing process, with changes as necessary. A second sheet of collagen biofabric is placed on the healing wound 4-5 weeks after the first application, in the same manner as the first application. If necessary, a third application is performed at the 8-9 week mark, and every 3-4 thereafter as needed.

5.5 Example 5

Treatment of Venous Leg Ulcer Patients with Collagen Biofabric

Several individuals having leg ulcers were treated with collagen biofabric in a non-clinical setting as follows.

Patient 1: Patient 1 presented with two venous leg ulcers on the ankle, one approximately 1 cm×1.5 cm, the other approximately 1.8 cm×1.3 cm. A 6×8 dry sheet of collagen biofabric was laid over both, and allowed to adhere by adsorption to the wound exudates. By six weeks post-application, the ulcers were completely healed.

Patient 2: Patient 2 presented with venous leg ulcers measuring approximately 2.2 cm×1.7 cm and 0.4 cm×1.0 cm. A 6×8 dry sheet of collagen biofabric was laid over both, and allowed to adhere by adsorption to the wound exudates. Two weeks after the initial sheet was applied, a second sheet was applied to the ulcers. A third application of a collagen biofabric sheet was made five weeks after the initial application. The ulcers were substantially healed by nine weeks after initial application.

Patient 3: Patient 3 presented with a venous leg ulcer, located proximate to the ankle, measuring 1.5 cm×0.9 cm. Treatment consisted of two applications of a dry collagen biofabric sheet, the second five weeks after the first. By eight weeks after the first application, the ulcer had epithelialized.

Patient 4: Patient 4 presented with a single venous leg ulcer measuring approximately 3.0 cm×1.5 cm. By six weeks after application of a single sheet of dry collagen biofabric, the ulcer had shrunk to approximately 1.8 cm×0.8 cm.

Patient 5: Patient 5 presented with a single venous leg ulcer measuring approximately 2.0 cm×1.2 cm. A single dry sheet of collagen biofabric was applied and allowed to allowed to adhere by adsorption to the ulcer exudates. After application, the collagen biofabric was moistened to that it adhered, as well, to the skin surrounding the ulcer. A dressing and compression were then applied. By 2 weeks post-application, the ulcer had noticeably diminished in size.

5.6 Example 6

Observational Use Study of Biofabric

A multicenter observational biofabric use study was conducted. The study concluded that collagen biofabric, applied as a dehydrated human amniotic membrane, is safe when used in the management of non-infected, full- or partial-thickness acute or chronic wounds.

Investigators were asked to enroll any patient who presented with a non-infected, full- or partial thickness wound which could have benefited from the biofabric, including acute or chronic wounds. As the study was observational, patients were not randomized, and there were no control groups. Patients with infected wounds, or with known hypersensitivity to the biofabric, were excluded from the study. Patients were evaluated for type of wound, safety (including number and type of adverse events), and efficacy of biofabric treatment. A total of 225 patients, exhibiting a total of 240 wounds, were treated in the study. A summary of enrolled patients is presented in Table 2. Although the study included patients having burns, collagen vascular disease wounds and acute wounds, only data relating to leg ulcers is presented in the tables herein.

TABLE 2

Patient wound types.

| Wound Type | Number of patients | Number of Wounds | Males N (%) | Females N (%) | Age at First Visit (average) | Age at First Visit (range) |
|---|---|---|---|---|---|---|
| Diabetic foot ulcers | 42 | 45 | 27 (64%) | 15 (36%) | 60.6 | 19.0-87.5 |
| Pressure ulcers | 22 | 22 | 15 (68%) | 7 (32%) | 66.2 | 30.8-89.8 |
| Arterial (ischemic) ulcers | 11 | 14 | 7 (64%) | 4 (36%) | 71.9 | 56.4-84.7 |
| Venous stasis ulcers | 78 | 85 | 42 (54%) | 36 (46%) | 64.2 | 28.7-88.6 |

N = number

Thirty five of the 42 patients with diabetic foot ulcers completed the study, as did 17 of the 22 patients with pressure (decubitus) ulcers, 10 of the 11 patients with arterial ulcers, and 67 of the 78 patients with venous leg ulcers.

Each of the patients participating in the study received at least one piece (6×8 cm) of the biofabric, applied directly to the wound. The biofabric was replaced when it appeared to have been absorbed into the wound. Where the wound presented dry, the wound was wetted with physiological sterile normal saline prior to applying the biofabric. The maximum number of pieces of biofabric applied to any one patient was 15. The maximum number of weeks any patient was treated with the biofabric was 27.7. The patient with the highest number of pieces applied for the longest time was one who had seven pieces applied over 15 weeks of treatment. Patient exposure to the biofabric is summarized in Table 3:

During the course of the study, 23 of the leg ulcer patients had adverse events, including 16 that developed wound infection, three that developed a worsening wound, three that developed cellulites at the wound site, and one that developed or experienced rash at the wound site. Six patients with leg ulcers experienced severe adverse events, apparently unrelated to the biofabric, during the course of the study. Three of these patients died, and one was hospitalized, for reasons unknown to the study organizers; one was hospitalized for peripheral vascular disease; and one experienced a cerebral vascular accident. In all, none of the adverse or severe adverse events was determined to be due to the use of the biofabric.

Although this observational study was primarily designed to capture safety and use information, some efficacy analyses were performed. Specifically, baseline wound surface areas (healers vs. non-healers), decrease in wound surface areas (healers vs. non-healers), and decrease in wound surface area over time were analyzed. Efficacy was determined by visual inspection of the wound(s) during the study. Patients that had a detectable reduction in the size of their wounds were deemed "healers," while those whose wounds did not appear to reduce in size were deemed "nonhealers". Table 4 summarizes wound size reduction in healers vs. nonhealers.

TABLE 3

Summary of exposure to collagen biofabric.

| Wound Type | N (wounds) | Number of weeks observed (range) | Number of weeks observed (average) | Number of 6 × 8 pieces applied (average) | Number of 6 × 8 pieces applied (range) | N exposed to 1 piece biofabric | N exposed to >1 piece biofabric |
|---|---|---|---|---|---|---|---|
| Diabetic foot ulcers | 45 | <1-25.3 | 9.5 | 2.8 | 1-15 | 14 | 31 |
| Pressure ulcers | 22 | 0.3-27 | 8.6 | 2.1 | 1-7 | 11 | 11 |
| Arterial (ischemic) ulcers | 14 | 1-25.5 | 11.7 | 2.5 | 1-6 | 5 | 9 |
| Venous stasis ulcers | 85 | 1-27.7 | 8.4 | 2.4 | 1-7 | 32 | 53 |

N = number

TABLE 4

Baseline wound surface areas by wound type.

| Wound Type | N (wounds) | Wounds healed N (%) | ALL WOUNDS Baseline wound surface area (cm²) Average (range) | HEALED WOUNDS Baseline wound surface area (cm²) Average (range) | NON-HEALED WOUNDS Baseline wound surface area (cm²) Average (range) |
|---|---|---|---|---|---|
| Diabetic foot ulcers | 45 | 15 (33%) | 8.0 (0.2-81.6) [6.3 (0.2-22.5)]* | 8.2 (0.2-81.6) [2.9 (0.2-10.3)]* | 8.2 (0.3-22.5) |

TABLE 4-continued

Baseline wound surface areas by wound type.

| Wound Type | N (wounds) | Wounds healed N (%) | ALL WOUNDS Baseline wound surface area (cm²) Average (range) | HEALED WOUNDS Baseline wound surface area (cm²) Average (range) | NON-HEALED WOUNDS Baseline wound surface area (cm²) Average (range) |
|---|---|---|---|---|---|
| [All diabetic foot ulcers except one outlier]* | | | | | |
| Pressure ulcers | 22 | 9 (41%) | 4.3 (0.75-22) | 1.4 (0.75-3) | 6.4 (0.8-22) |
| Arterial (ischemic) ulcers | 14 | 5 (36%) | 20.8 (1.2-108) | 3.1 (1.2-6.4) | 30.6 (1.4-108) |
| Venous stasis ulcers | 85 | 36 (42%) | 13.3 (0.06-203) | 5.2 (0.4-40) | 18.8 (0.06-203) |

N = number
*Upon further clinical evaluation, one wound, classified by the investigator as a diabetic foot ulcer with a surface area of 81.6 cm², appeared to be a post-operative wound located on the calf of a diabetic patient. Therefore, a separate efficacy calculation was made excluding this wound.

Decreases in wound surface area for healers, decreases in wound width, and decreases in wound surface area over time observed for all wounds by wound types, are presented in Tables 5-7, below.

TABLE 5

Decrease in wound surface area by wound type (healers)

| Wound Type | N (wounds) | Wounds healed N (%) | Baseline wound surface area (cm²) Average (range) | Weeks to heal Average (range) | Rate of healing (cm²/week) Average (range) |
|---|---|---|---|---|---|
| Diabetic foot ulcers | 45 | 15 (33%) | 8.2 (0.2-81.6) | 8.4 (3-25.3) | 1.1 (0.03-11.7) |
| Pressure ulcers | 22 | 9 (41%) | 1.4 (0.25-3) | 8.3 (2-19) | 0.23 (0.02-0.43) |
| Arterial (ischemic) ulcers | 14 | 5 (36%) | 3.1 (1.2-6.4) | 6.0 (2.5-12) | 0.73 (0.13-1.8) |
| Venous stasis ulcers | 85 | 36 (42%) | 5.2 (0.4-40) | 7.3 (2-27.7) | 1.1 (0.05-10.8) |

N = number

TABLE 6

Decrease in wound width (for healers) by wound type

| Wound Type | N (wounds) | Wounds healed N (%) | Baseline wound width (cm) Average (range) | Weeks to heal Average (range) | Rate of decrease in width (cm/week) Average (range) |
|---|---|---|---|---|---|
| Diabetic foot ulcers | 45 | 15 (33%) | 1.3 (0.4-3.4) | 8.4 (3-25.3) | 0.20 (0.03-0.63) |
| Pressure ulcers | 22 | 9 (41%) | 0.97 (0.5-1.5) | 8.3 (2-19) | 0.17 (0.04-0.33) |
| Arterial (ischemic) ulcers | 14 | 5 (36%) | 1.36 (0.8-2) | 6.0 (2.5-12) | 0.34 (0.09-0.76) |
| Venous stasis ulcers | 85 | 36 (42%) | 1.6 (0.4-5) | 7.3 (2-27.7) | 0.33 (0.04-1.7) |

N = number

TABLE 7

Decrease in wound surface area over time for all wounds by wound type.

| Wound Type | N (wounds) | Baseline wound surface area (cm$^2$) Average (range) | Final wound surface area (cm$^2$) Average (range) | Weeks observed Average (range) | Rate of healing (cm$^2$/week) Average (range) |
|---|---|---|---|---|---|
| Diabetic foot ulcers | 45 | 8.0 (0.20-81.6) | 3.4 (0-22.5) | 9.5 (0-25.3) | 0.6 (−1.8-11.7) |
| Pressure ulcers | 22 | 4.3 (0.25-22) | 2.8 (0-22.5) | 8.6 (0.3-27) | 0.31 (−0.28-2.9) |
| Arterial (ischemic) ulcers | 14 | 20.8 (1.2-49) | 15.2 (0-82.7) | 11.7 (1-25.5) | 0.56 (−1.3-1.8) |
| Venous stasis ulcers | 85 | 13.3 (0.06-202.5) | 6.8 (0-69.9) | 8.4 (1-27.7) | 0.80 (−3.2-10.8) |

N = number

One wound type subgroup, venous stasis ulcers, was examined in detail. Outcomes for this group are summarized in Table 8.

TABLE 8

Venous stasis ulcer (VSU) summary.

| | All VSU (N = 85) | Healed VSU (42%) (N = 36*) | Non-healed VSU (56%) (N = 48*) |
|---|---|---|---|
| Patients treated (N) | 78 | N/A | N/A |
| Completed patients (N) | 67 (85%) | 31 | 36 |
| Discontinued patients¶(N) | 11 (14%) | 0 | 10 |
| Age (mean years) | 64.2 | 65.3 | 63.9 |
| Weeks to healing (mean) | N/A | 7.3 | N/A |
| Weeks to healing (median) | N/A | 5.5 | N/A |
| Rate of healing (cm$^2$/week) | N/A | 1.8 | N/A |
| Weeks of observation (mean) | 8.4 | 7.3 | 9.3 |
| Weeks of observation (range) | 1-27.7 | 2-27.7 | 1-21.6 |
| Mean wound baseline surface area (cm$^2$) (all wounds) | 13.3 | 5.2 | 18.8 |
| Median wound baseline surface area (cm$^2$) | 4.8 | 2.7 | 9.0 |
| Pieces biofabric used (N) | 2.4 | 2.2 | 2.5 |
| Wounds treated with 1 piece biofabric (N) | 32 | 15 | 16 |
| # Wounds treated with >1 piece biofabric (N) | 53 | 21 | 32 |
| SAEs (N)† | 4 | 0 | 4 |
| AEs (N)‡ | 9 | 1 | 8 |

AE = Adverse event; SEA = severe adverse event; N = number; N/A = not applicable.
*One patient was lost to follow-up prior to final wound healing determination.
¶Lost to follow up (N = 5), adverse event (N = 5), withdrew consent (N = 1).
†Hospitalization for unknown reason (N = 2), death, cause unknown (N = 1).
‡Wound infection (N = 5), worsening wound (N = 1), cellulitis (N = 1), rash (N = 1).

Conclusions: The collagen biofabric (dried amniotic membrane) was shown to be safely applicable to patients having the four major leg ulcer types. Multiple pieces of the biofabric could safely be applied to non-infected, partial- or full-thickness chronic wounds. Leg ulcers, particularly venous leg ulcers, can be considered non-healing wounds. Thus, though not an efficacy study, the study data indicate that this collagen biofabric be useful in the treatment or management of leg ulcers.

Equivalents:

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method of treating a leg ulcer, comprising contacting said ulcer with a first collagen biofabric for a first period of two to five weeks, followed by contacting said ulcer with a second collagen biofabric for a second period of time, wherein said contacting with said first or second collagen biofabric improves at least one aspect of the leg ulcer, or prevents or reduces the worsening of at least one aspect of the leg ulcer, wherein the first and second collagen biofabric is decellularized and dehydrated prior to contacting said ulcer.

2. The method of claim 1, wherein said first or second collagen biofabric is not artificially crosslinked.

3. The method of claim 1, wherein said first or second collagen biofabric is not protease-treated during production.

4. The method of claim 1, wherein said contacting for the first period of time or the second period of time is for a time sufficient for at least one aspect of the leg ulcer to measurably improve compared to a leg ulcer not contacted with the collagen biofabric.

5. The method of claim 1, wherein said contacting for the first period of time or the second period of time is for a time sufficient to prevent or reduce the worsening of at least one aspect of a leg ulcer.

6. The method of claim 1, wherein said leg ulcer is a venous leg ulcer, arterial leg ulcer, diabetic leg ulcer or decubitus ulcer.

7. The method of claim 1, wherein said leg ulcer is a venous leg ulcer.

8. The method of claim 1, wherein said first or second collagen biofabric is provided as a sheet or membrane.

9. The method of claim 1, wherein said first or second collagen biofabric is provided as a netting or webbing.

10. The method of claim 1, wherein said first or second collagen biofabric is mounted on a support.

11. The method of claim 10, wherein said support is a bandage.

12. The method of claim 1, wherein said contacting comprises placing the collagen biofabric on the leg ulcer so that substantially all of the surface area of the biofabric contacts the leg ulcer.

13. The method of claim 1, wherein said first or second collagen biofabric additionally comprises a bioactive compound not naturally-occurring in the collagen biofabric, or present in a different concentration than in collagen biofabric to which the bioactive compound has not been added.

14. The method of claim 13, wherein said bioactive compound is a small organic molecule, an antibiotic, pain medication, anti-inflammatory agent, cytokine, growth factor, enzyme inhibitor, kinase inhibitor, an anti-tumor agent, an anti-fungal agent, an anti-viral agent, an anti-infective agent, a wound sealant or a wound healing or sealing agent.

15. The method of claim 14, wherein said wound healing or sealing agent is platelet-derived growth factor (PDGF), transforming growth factor (TGF), thymosin, hyaluronic acid, fibrin, fibronectin or thrombin, or a combination thereof.

16. The method of claim 1, wherein the first period of time is four to five weeks.

* * * * *